US012203111B2

(12) United States Patent
Goebl et al.

(10) Patent No.: US 12,203,111 B2
(45) Date of Patent: Jan. 21, 2025

(54) **MATERIALS AND METHODS FOR CREATING STRAINS OF *Saccharomyces cerevisiae* THAT EXHIBIT AN INCREASED ABILITY TO FERMENT OLIGOSACCHARIDES INTO ETHANOL**

(71) Applicants: Xylogenics, Inc., Indianapolis, IN (US); Mark Goebl, Indianapolis, IN (US); Joshua Heyen, Brownsburg, IN (US); Nadaraj Palaniappan, Carmel, IN (US); Ross Cocklin, Keene, NH (US); Kathryn Houin, Lebanon, IN (US); Matthew Kelker, Zionsville, IN (US)

(72) Inventors: Mark Goebl, Indianapolis, IN (US); Joshua Heyen, Brownsburg, IN (US); Nadaraj Palaniappan, Carmel, IN (US); Ross Cocklin, Keene, NH (US); Kathryn Houin, Lebanon, IN (US); Matthew Kelker, Zionsville, IN (US)

(73) Assignee: Xylogenics, Inc., Indianapolis, IN (US)

( * ) Notice: Subject to any disclaimer, the term of this patent is extended or adjusted under 35 U.S.C. 154(b) by 865 days.

(21) Appl. No.: 17/261,454

(22) PCT Filed: Jul. 19, 2019

(86) PCT No.: PCT/US2019/042605
§ 371 (c)(1),
(2) Date: Jan. 19, 2021

(87) PCT Pub. No.: WO2020/018905
PCT Pub. Date: Jan. 23, 2020

(65) Prior Publication Data
US 2021/0309982 A1  Oct. 7, 2021

Related U.S. Application Data

(60) Provisional application No. 62/700,679, filed on Jul. 19, 2018.

(51) Int. Cl.
*C12N 9/24* (2006.01)
*C12N 15/52* (2006.01)

(52) U.S. Cl.
CPC .......... *C12N 9/2402* (2013.01); *C12N 15/52* (2013.01); *C12Y 302/0102* (2013.01)

(58) Field of Classification Search
CPC ...... C12N 9/2402; C12N 15/52; C12N 15/90; C12Y 302/0102; C12P 7/06; C07K 14/395
See application file for complete search history.

(56) References Cited

U.S. PATENT DOCUMENTS

2018/0010151 A1  1/2018 Verwaal et al.

FOREIGN PATENT DOCUMENTS

| EP | 0323838 B1 | 5/1995 |
| JP | 2007082431 A | 4/2007 |
| WO | WO-2004/079008 A1 | 9/2004 |
| WO | WO-2017/106739 A1 | 6/2017 |
| WO | 2018046821 A1 | 3/2018 |

OTHER PUBLICATIONS

Charron et al. "The Naturally Occurring Alleles of MAL1 in *Saccharomyces* Species Evolved by Various Mutagenetic Processes Including Chromosomal Rearrangement", Genetics, 1988, vol. 120, Issue 1, pp. 83-93. (Year: 1988).*
Alves-Jr et al. "Maltose and Maltotriose Active Transport and Fermentation by *Saccharomyces cerevisiae*", Journal of American Society of Brewing Chemists, 2007, vol. 65, Issue 2, pp. 99-104). (Year: 2007).*
Teste et al. "Characterization of a New Multigene Family Encoding Isomaltases in the Yeast *Saccharomyces cerevisiae*, the IMA Family ", Journal of Biological Chemistry, 2010, vol. 285, No. 35, pp. 26815-26824. (Year: 2010).*
Duina et al. "Budding Yeast for Budding Geneticists: A Primer on the *Saccharomyces cerevisiae* Model System", Genetics, 2014, vol. 197, Issue 1, pp. 33-48. (Year: 2014).*
Seker "Multiple clustering models and SVD-QR-based method for reliable gene expression profile analysis", 2006, Conference paper, 6 pages. (Year: 2006).*
Extended European search report issued in European patent application No. 19837401.9, dated Mar. 25, 2022.
Database EMBL [Online] Apr. 10, 1996, DOI; 10.1002/(SICI)1097-0061 (Mar. 15, 1997) 13:3251::AID-YEA633.3.CO;2-I.:"*S. cerevisiae* DNA for fragment from chromosome VII", XP55899332, retrieved from EBI accession No. EM_STD:X94332 Database accession No. X94332.
Charron, Maureen J., et al., "The Naturally Occurring Alleles of MAL1 in Saccharomyces Species Evolved by Various Mutagenic Processes Including Chromosomal Rearrangement," Genetics Society of America, vol. 120, Sep. 1988, 11 pages.
Teste, Marie-Ange, et al., "Characterization of a New Multigene Family Enclonding Isomaltases in the Yeast *Saccharomyces cerevisiae*, the IMA Family," The Journal of Biological Chemistry, vol. 285, No. 35, Aug. 27, 2020. 11 pages.
Volckaert, Guido, et al., "Sequence Analysis of a Near-subtelomeric 35.4 kb DNA Segment on the Right Arm of Chromosome VII from *Saccharomyces cerevisiae* Carrying the MAL1 Locus Revals 15 Complete Open Reading Frames, Including ZU01, BGL2, and BIO2 Genes and the ABC Transporter Gene," Yeast Sequencing Reports, vol. 13, (1997). 17 pages.

(Continued)

*Primary Examiner* — Louise W Humphrey
*Assistant Examiner* — Deepa Mishra
(74) *Attorney, Agent, or Firm* — Faegre Drinker Biddle & Reath LLP

(57) ABSTRACT

Disclosed herein is a yeast strain capable of fermenting high maltose syrups into ethanol in the presence of glucose. In commercially important fuel ethanol yeast strains, the presence of glucose prevents robust maltose fermentation. This invention causes enhanced co-fermentation of maltose and glucose in strains otherwise identical to commercial fuel ethanol yeast strains.

8 Claims, 24 Drawing Sheets

Specification includes a Sequence Listing.

(56) References Cited

OTHER PUBLICATIONS

Yue, Jia-Xing, et al., "Contrasting evolutionary genome dynamics between domesticated and wild yeasts," Nature Genetics, vol. 49, No. 6, Jun. 2017, 17 pages.
International Search Report and Written Opinion issued by the ISA/US, Commissioner for Patents, dated Nov. 1, 2019, for International Application No. PCT/US2019/042605, 11 pages.

* cited by examiner

SEQUENCE LISTING

<160> NUMBER OF SEQ ID NOS: 6

<210> SEQ ID NO 1
<211> LENGTH: 8738
<212> TYPE: DNA
<213> ORGANISM: Saccharomyces cerevisiae

<400> SEQUENCE: 1

```
caccccagcc atcgtcatta gagtctttga aacttgctgg gtaaatttga tagaacgtgg     60
cctcttccca ccactttggt tctgtctctg gatgtgcaga agaaatagtc atcgatagta    120
aatattacgt tgaaaagctt tgtttgtatc ttgtttgatc tgtgcttgct cgattaattt    180
gagacagctt ttttatttca aaacaggcgt ctaaccaaac gtctagcaac tcaatatcat    240
tgcccttaag tacttttttat ttcaaaagga gatcctttct cattctgggg taaactatgg    300
tatgacgaaa accatgaaaa ataaggaaca taatttatcc gagtatttca acgatcccaa    360
gtactgacat aaactttagt agccaattta tagcgtgggg tgcctacttc gtcacatttg    420
atatcgtaca gcgaaaaaac attagtaact ttatttcctt atttcagggc cacttttctc    480
gagaataacg ctgcgtgctg agcggttgtt cacaccgcgg agttggaaac tttattctcc    540
gaaatattct ccccactaaa atatccttac gtattgtgaa acttagtttt cttttttgtat    600 tagggtgtaa tttcttattt tccctgtatt tcaccgcatg caaattctta cgatatttac    660
tccggtaaac gcagttaaga gctattgtcc ggtccgactg aatgaatatt cggttagaaa    720
cgcatatttg tggggaaata acaacctcaa agatatagac ggagcagtac cgtaaggttt    780
acagaatggc atgaccaccc acaataaagc aaggacctcg agacacatgc ctttcaaaat    840
agaaataaag gttttcgaac atcattttc gcttgttgta tagtagtctt tacagtaaca    900
gtgcatctga gtacaggaac gattgtcttg ataatatgtg aaaagtgcac acaaaattag    960
agggtgtcct ttacaagtat tcttagaaac acattcaaga gcacaaaagt cgatgcttta   1020
agggtcaagg tggtggaaaa cttgactgga attcttgacg aaaaaacaag aaaaacgtga   1080
```

```
ttcgagcaat cataaacata cagccccgtt ccaaccggat cttgaggttt cccatttttag    1140 atggaaataa gcagagcaaa ataaaaatct tgaacaagta atagtggtga ctgcaggtta    1200
cgttggcata taaagtccgg gtgacctggg tttcctgcac caccagcccc catatgctag    1260
cacaatgggt tttctttatc cccggtcata attactcatt ttgctatatt cttcataact    1320
taagtacgca gatagagaaa attaataatc tcgatatata ttaaagtaaa tgaaaagtag    1380
aaaatttagc cagaactctt ttttgcttcg agtatgactt taactaagca acatgcgcc     1440 aagcaggcat gcgactgctg tcgtattcgt cgagtgaaat gcgatggtaa aaggccgtgt    1500
agcagttgcc tacagaatag tttggattgc acttatctgc aaccgtcgag aaaaagaggt    1560
ccgaagtcca ttaggttgag gagcttgaaa agaatagcag aagtgcagag ggaaagcggt    1620
cctaacacca ttgcaactgc tcctgtaata tataagaggg ttcccaaaaa gctaatcgat    1680
cagtgcttgc ggctctatca cgataattta tacgtaatct ggccccttct ttcgtacgat    1740
gaccttcaca aacttctgga ggaaaaatac aatgacaatt acgtatattg gtttctgacc    1800
gctttatcag cggccaccct cagtgattta caaactgaaa taaaatctga agaggaagtc    1860
actttcacgg gaaaacggtt atctaatctt tgcatctcat cgtgtcagca attcgacgat    1920
ttggataaca gcaatatatt caatattatg acgtactact gtttgcatcg tagctttgca    1980
caaatatcga acgcaagaac ttcttacaga ctctgttgtg aagcggtcgg tctgattacg    2040
gtagcagggt tacatcggga agaaacttac ggatcccta catttgaaga acagcaactt     2100
agacggaaac tttattactt gcttctcatg acggagagat actatgccat atatcttcat    2160
tgtgcgacga gcctggatgc cacaatagca ccaccgcaac ttgaacttgt aactgatcct    2220
cagctttcta tggacagttt ccttgaaatg attagggtat ttactgtacc aggaaaatgt    2280
ttcttcgatg ctttagccgc tgactctaca gatgcttctt gcactgaaga gtcattgaaa    2340
aagatatgga aagagctcca tacagcatca ttagaaatag agccgtggtc ttacggttac    2400
gttgacattg cattttccag gcactggatt agagtcctcg cttggaagct agtcttgcgg    2460
acaggaaata tcaacttcct atccgcctct aacagtgcac atgtaccact tgaaattgca    2520
agggatatgc ttgacgacgt gtttctaaca ccaaataatc tttatggagt tcatggcccct   2580 gggataccaa caaaggcaat agaagtagcc aatgcactag tggatgtcat gaatcagtat    2640
gatcaagata ctgaatcaga ggcttggaaa gttttgtgcg aaatttccaa atttgtcttc    2700
tcttaaaaac aatacgatgg aaaactggtt gaaaattttg tgactaaatg tcagagcgct    2760
cttattactc ttccaatctc taaacctttg aaaaaaaatg aagatttgca taaaatatga    2820
ctcactttaa tttcttgagt gaacattttt catccatttc ttcatgtaaa ctccaaaaaa    2880
gaaagcttct gtcggtttta agataaaagt actcctcgtg tataggaata tttttatctt    2940
tgttagctct gtagaaaaag atacagataa agctcctgta atatttgttg cagattttg     3000 gtccatgaat tattttatca cgatcgaaaa gaagttatgt tcgttatatc cagtggaaaa    3060
agcattgtta tatgatggag tccggtgcct gtctctgcat aaaaaaataa cattttaata    3120
catgggaggt gttatattgt acagagagga gacaatgata tggctttgtt ggtgttgtat    3180
gactaacata gggcgttttt atgattcatg aaatttattt aatacatgtt tacgatttta    3240
actattgtga atacattgct attgtatata tgtaatcata tcagcaattc tagcatttta    3300
acatgtgact tgagctggat gattaaaata tgttaatttt tttagaatta ttatctagta    3360
caacaactac cagaatagtt gaactgaata atatcaaatg aaaaggactc ctctagctga    3420
```

```
attttggaat gtttgccaaa taaaaaaaag actttataac aaaaggttaa ttaaatgtat    3480
ttagtaaaaa aaaaaaagtt tgtcatattt atctattgaa atgaagtatc atttgttcac    3540
aacagatgag gtgcttcgcc cttcatctac cacagaagtt tccaaatctt ccttcggatc    3600
tttaacatta atttctgcag ctgctgcttt ggcagctgca aaagggtcga ctttagtcga    3660
cttgaacttt cttgctggaa caccaagtct aaacaattca tttatctcaa taaaagtcct    3720
gccagcggtt tctggtaaat cgacaacagc ccaagctaaa gtggccagac aaaatcctcc    3780
ccagaaaaag cctgatttag cacccccaatt ccatttctct gagttcaatt ggtacatgat    3840
caaaactgta actacaactt ggatcacatt gtaagcatta cgagccaaaa taattgtttt    3900
ggttcttagc cttgaagacg gtatttcaga cactaagcaa aaaacaacag gtgcaatacc    3960
gaggttgtaa aagaacgcga caaccattag aagagcacca ctacccattt tagcgccatg    4020
agtgtctgaa catcctaaac caccgataat gaagaacata atagcctgaa aagccagccc    4080
aaaagcataa aggtcaaatc tgccacaata ttttgaagcc caccaggata taaacgttgc    4140
agcaatacca agacaatatt ggataatact gaaagtaaaa gccgtatcag tgctaacacc    4200
agcttttttca taaagtaagg ttgaataacc aattaatgat gcaccacagg agcattgacc    4260
gatccaacat aaacaagcta ttctcgttct tctcctgtta ataccatctt tcacacaatc    4320
ccagtaagtt ccttcatcag acattttctg ctccttttct atagtagttt tgattttatc    4380
gagttccata ctcactagta attctttctc gggtccttta ccacttaatg ttctttcaag    4440
tgatctcctc gcttgatcaa tccttccttt tttaaccagc caccatggag actctggtgc    4500
aaaaaaaata cctaccgcca aaggaagggg ccagatccac tgcaaagcaa aaggtagctt    4560
atatcctagt tctgagttgg catatttgtt ctgggaattt ttcataatac cagcagcgaa    4620
aagttgaccg aacgcccaac ataaattaga ataagtcgtc aaatagtatc ttagggccaa    4680
aggacaaatt tcagaagcat aagaaacggt caaacattgg aaacaacccc atggcatacc    4740
acacaatgcc tgtcccacgg caatcatacc caaactcttg caaaaataca gaatgaaaat    4800
gaaagccgct aaaaagaaca acgccatgat cagagtgtaa cggttgccca tgtaatctac    4860
agaaggccca gtcatttgca aaccgacaat ctcacctgcc atgtagcata gacatagacc    4920
gatttgccag gaaactgaaa tttcataatc tcctgtattg ctattcaaag aaccatattt    4980
tttttgaaaa acaggcaggg catagaaagc tcctagaatg gctgtgtcat aaccctcttg    5040
aatcaatgtt gtggaaacta atagtgacca agcagcagct tttggatatg tcttcaaagc    5100
tgtcatgagt ggcattcccc tctcactttc atctgcctct ttggcgtcct gcatagcttc    5160
atcgagaagg tcggggactt cttcattatt atcgtttggt attagtgaac ctggaccgta    5220
ctcaagatgg gaaagatcaa aatcactttt cttaccttgc tcctccatct ctatcgagtt    5280
gaattcggta gcgttcacgc cattctcgat ctcatctaag tgtgagtcgt tcctgtcttt    5340
ttttctgttt attaatgagg ataatcccctt catagttaat taatagtctt ggatgtaatt    5400
cttattgtta tactgaatat gctaaaacca ctcacaacaa gtatggagta tattgtgcct    5460
ctttatatcc tgagtactta tgcaatatgc gctcactcag gatgaaatgt acacagccga    5520
aagtatattg aaagctgcct ctgcggaaac ttctatctaa tgttgtctcc agatgtagac    5580
tatgaggcct gaagaagtct ttaagcacct gttggagagt ataaggagac tgctacaaca    5640
acgtcttccc cacaaaaaat tatgtggagg ccgctatgat acctgcacaa acgttaagtt    5700
acacatgaaa aagagactga cataactttg atctctgaaa atatgttttc cccgagtagc    5760
ttcactgctt ggataccaat acgaatagac cttggctata gtaagttgcc tctgtaccgt    5820
```

```
agagattctt gcaacctcgc ttaaactctc gcttttatca aatttcgcta aacacggggt    5880
ttaagttaaa gtttacagga tttatccgga aattttcgcg gaccccacac aattaagaat    5940
tggctcgaag agtgataacg catacttttc ttttcttttt ttagttccta gcgtacctaa    6000
cgtaggtaac atgatttgga tcgtgggatg atacaaacaa cgtaagatga atagttcctt    6060
cctcaattct tcttgcagca tcattttctt gaggcgctct gggcaaggta taaaagttc     6120 cattaatacg tctctaaaaa attaaatcat ccatctctta agcagttttt ttgataatct    6180
caaatgtaca tcagtcaagc gtaactaaat tacataaatg actatttctg atcatccaga    6240
aacagaacca aagtggtgga aagaggccac aatctatcaa atttacccag caagttttaa    6300
agactccaat aacgatggct ggggtgattt aaaaggtatc acttccaagt tgcagtatat    6360
taaagatctt ggcgttgatg ctatttgggt ttgtccgttt tatgactctc ctcaacaaga    6420
tatggggtat gatatatcca actacgaaaa ggtctggccc acatacggta ccaatgagga    6480
ctgttttgag ctaattgaca agactcataa gctgggtatg aaattcatca ccgatttggt    6540
tatcaaccac tgttctacag aacacgaatg gttcaaagag agcagatcct cgaagaccaa    6600
tccgaagcgt gactggttct ctggagacc  tcctaagggt tatgacgccg aaggcaagcc    6660
aattcctcca aacaattgga aatctttctt tggtggttca gcttggactt ttgatgaaac    6720
tacaaatgaa ttttacctcc gtttgtttgc gagtcgtcaa gttgacttga attgggagaa    6780
tgaagactgc agaagggcaa tctttgaaag tgctgttgga ttttggctgg accatggtgt    6840
agatggtttt agaatcgata ccgctggttt gtattcgaaa cgtcctggtt taccagattc    6900
cccaattttt gacaaaacct cgaaattaca acatccaaat tgggggtctc acaatggtcc    6960
taggattcat gaatatcatc aagaactaca cagatttatg aaaaacaggg tgaaagatgg    7020
tagagaaata atgacagtcg gtgaagttgc ccatggaagt gataatgctt tatacaccag    7080
tgcagctaga tacgaagtca gcgaagtttt ctccttcacg cacgttgaag ttggtacctc    7140
gccatttttc cgttataaca tagtgccctt caccttgaaa caatggaaag aagccattgc    7200
atcgaacttt ttgttcatta acggtactga tagttgggct accacctaca tcgagaatca    7260
cgatcaagcc cggtcaatta cgagatttgc tgacgattcg ccaaagtacc gtaaaatatc    7320
tggtaagctg ttaacattgc tagaatgttc attgacaggt acgttgtatg tctatcaagg    7380
tcaggagata ggccagatca atttcaagga atggcctatt gaaaagtatg aggacgttga    7440
tgtgaaaaac aactacgaga ttatcaaaaa aagttttggt aaaaactcga aggaaatgaa    7500
ggattttttt aaaggaatcg ccctactttc tagagatcat tcgagaactc ccatgccatg    7560
gacgaaagat aagcccaatg ctggatttac tggcccagat gttaaacctt ggttttctct    7620
gaatgaatct ttcgagcaag gaatcaatgt tgagcaggaa tccagagatg atgactcagt    7680
tctcaatttt tggaaaaggg ccttgcaagc cagaagaaaa tataaggaac ttatgattta    7740
tggttacgat ttccaattca ttgatttaga cagtgaccag atcttagct  tcactaaaga    7800 gtacgaagac aagacgctgt tgctgctttt aaatttcagt ggcgaagaaa ttgaattcag    7860
cctcccaaga gaaggtgctt ctttatcttt tattcttgga aattatgatg atactgacgt    7920
ttcctccaga gttttgaaac catgggaagg tagaatctac ctcgtcaaat aaaattagtg    7980
ccggcttttt tttagcgcgt actttaacga aataacacat gattttcac  atgatttttg    8040 ttagataaat ttttatatg  taaatgatga tagcgtaaaa gcactgttga taatttgttt    8100
caccattatg ggtaaatgtg ttttctaca  tgaccctcgt tcattatgat atttagcgtg    8160
```

-continued

| | |
|---|---|
| tatataaatg tgaattccaa attattaatg aggcataaga agcactatcc tttctcttcg | 8220 |
| gatgaaaaca agggagaaga aacctgtgct ggtattaatg ctgaaatgtc ttgctaagaa | 8280 |
| tcatacaagg tggtagtttt atttaataaa gaaagaaaa ggactagata taaaaagtga | 8340 |
| aatgaatata agatagcgtt aagagatgtc cgcagtactt gacacataat ttagcgtttt | 8400 |
| ctcgggaagc tctgtgattt tatgattcaa taacacagcg taattgattt cgtgatagtt | 8460 |
| cgatcctata tgtaatctca cgtaacactc aggcgagtta caaatcgat tcaacattgc | 8520 |
| cggcttatgc gtttacgtca agtctgagca tgcctacccc cttccgaacc cgccttttat | 8580 |
| tgtctagcct tcagatgaac taaaccaatc atctgtccat aattcctctg ctttagacag | 8640 |
| tgttattaag caaaagaaaa taagcgcata agattcttgc tacttcagta actccacaac | 8700 |
| attaacaccc cacaatcaat atctaaaagc caatgaag | 8738 |

<210> SEQ ID NO 2
<211> LENGTH: 9216
<212> TYPE: DNA
<213> ORGANISM: Artificial Sequence
<220> FEATURE:
<223> OTHER INFORMATION: Vector sequence with MAL1 gene cluster from
      Cen.PK strain 113-7D

<400> SEQUENCE: 2

| | |
|---|---|
| acaggaacga ttgtcttgat aatatgtgaa aagtgcacac gaaattagag ggtgtccttt | 60 |
| acaagtattc ttagaaacac attcaagagc acaaaagtcg atgctttaag ggtcaaggtg | 120 |
| gtggaaaact tgactggaat tcttgacgaa aaaacaagaa aaacgtgatt cgagcaatca | 180 |
| taaacataca gccccgttcc aaccggatct tgaggtttcc cattttagat ggaaataagc | 240 |
| agagcaaaat aaaaatcttg aacaagtaat agtggtgact gcaggttacg ttggcatata | 300 |
| aagtccgggt gacctgggtt tcctgcacca ccagccccca tatgctagca caatgggttt | 360 |
| tctttatccc cggtcataat tactcatttt gctatattct tcataactta agtacgcaga | 420 |
| tagagaaaat taataatctc gatatatatt aaagtaaatg aaaagtagaa aatttagcca | 480 |
| gaactctttt ttgcttcgag tatgacttta actaagcaaa catgcgccaa gcaggcatgc | 540 |
| gactgctgtc gtattcgtcg agtgaaatgc gatggtaaaa ggccgtgtag cagttgccta | 600 |
| cagaatagtt tggattgcac ttatctgcaa ccgtcgagaa aaagaggtcc gaagtccatt | 660 |
| aggttgagga gcttgaaaag aatagcagaa gtgcagaggg aaagcggtcc taacaccatt | 720 |
| gcaactgctc ctgtaatata taagagggtt cccaaaaagc taatcgatca gtgcttgcgg | 780 |
| ctctatcacg ataatttata cgtaatctgg ccccttcttt cgtacgatga ccttcacaaa | 840 |
| cttctggagg aaaaatacaa tgacaattac gtatattggt ttctgaccgc tttatcagcg | 900 |
| gccaccctca gtgatttaca aactgaaata aaatctgaag aggaagtcac tttcacggga | 960 |
| aaacagttat ctaatctttg catctcatcg tgtcagcaat ttgacgattt ggataacagc | 1020 |
| aatatattca atattatgac gtactactgt ttgcatcgta gctttgcaca atatcgaac | 1080 |
| gcaagaactt cttacagact ctgttgtgaa gcggtcggtc tgattacggt agcagggtta | 1140 |
| catcgggaag aaacttacgg atcccttaca tttgaagaac agcaacttag acggaaactt | 1200 |
| tattacttgc ttctcatgac ggagagatac tatgccatat atcttcattg tgcgacgagc | 1260 |
| ctggatgcca caatagcacc accgcaactt gaacttgtaa ctgatcctca gctttctatg | 1320 |
| gacagtttcc ttgaaatgat tagggtattt actgtaccag gaaaatgttt cttcgatgct | 1380 |
| ttagccgctg actctacaga tgcttcttgc actgaagagt cattgaaaaa gatatggaac | 1440 |

```
gaactccaca caacttcctc ggaaatagag ccatggtcta acggttacat agacatctca    1500
ttttcccggc attggattag gatactagca tggaagctag cttatcaaat gaggggtagc    1560
aacttttcat tgaacgctaa caatgggcaa ataccaatag aaattgcgag agatatgtta    1620
atagacactt acttaacccc agagaatctt tacgatgtcc atggtcccgg ggtaccagtg    1680
aaaacattag aaatagctac tgctttggtg gacattgtag gccagtatga tcataacatg    1740
aaattagaag catggaatgt tttgcatgat gtatgcaaat ttgcttttc tttaaaccac      1800 tataacaatg atatgctgaa gagattttcc accaaatgcc agaatgccct aattactctg    1860
cccatttcta aacctttaca attggatggt tatcccaagg ataatgaaga catagaccct    1920
tgattaattt tcattttgt gcatctcaac ttcctggtaa gtgatagctt tccattgtag     1980
aaactgtgtt tccgcaacac aagggtaaaa ttcactgcta attgcgaccc atttcatga      2040 acagagtaat taattttcta tttggaggtc tacttttaca agtataagac tgcttcttac    2100
catgatgtct ccctattgaa aattatattt aataaaatac ttttaggcac gctaacgtta    2160
gcattcttcc cagaattcct atactaacag ttttcagtat atatacactt ttttactgag    2220
tgctaagagc cagattggat gagatgattg tgtactgatg gagaattaac ggttggagag    2280
ctattactca cataacttcg tataatgtat gctatacgaa gttatttagc ttgcctcgtc    2340
cccgccgggt cacccggcca gcgacatgga ggcccagaat accctccttg acagtcttga    2400
cgtgcgcagc tcaggggcat gatgtgactg tcgcccgtac atttagccca tacatcccca    2460
tgtataatca tttgcatcca tacattttga tggccgcacg gcgcgaagca aaaattacgg    2520
ctcctcgctg cagacctgcg agcagggaaa cgctcccctc acagacgcgt tgaattgtcc    2580
ccacgccgcg cccctgtaga gaaatataaa aggttaggat ttgccactga ggttcttctt    2640
tcatatactt cctttaaaaa tcttgctagg atacagttct cacatcacat ccgaacataa    2700
acaaccatgg gtaaaaagcc tgaactcacc gcgacgtctg tcgagaagtt tctgatcgaa    2760
aagttcgaca gcgtctccga cctgatgcag ctctcggagg gcgaagaatc tcgtgctttc    2820
agcttcgatg taggagggcg tggatatgtc ctgcgggtaa atagctgcgc cgatggtttc    2880
tacaaagatc gttatgttta tcggcacttt gcatcggccg cgctcccgat tccggaagtg    2940
cttgacattg gggaattcag cgagagcctg acctattgca tctcccgccg tgcacagggt    3000
gtcacgttgc aagacctgcc tgaaaccgaa ctgcccgctg ttctgcagcc ggtcgcggag    3060
gccatggatg cgatcgctgc ggccgatctt agccagacga gcgggttcgg cccattcgga    3120
ccgcaaggaa tcggtcaata cactacatgg cgtgatttca tatgcgcgat tgctgatccc    3180
catgtgtatc actggcaaac tgtgatggac gacaccgtca gtgcgtccgt cgcgcaggct    3240
ctcgatgagc tgatgctttg ggccgaggac tgccccgaag tccggcacct cgtgcacgcg    3300
gatttcggct ccaacaatgt cctgacggac aatggccgca taacagcggt cattgactgg    3360
agcgaggcga tgttcgggga ttcccaatac gaggtcgcca acatcttctt ctggaggccg    3420
tggttggctt gtatggagca gcagacgcgc tacttcgagc ggaggcatcc ggagcttgca    3480
ggatcgccgc ggctccgggc gtatatgctc cgcattggtc ttgaccaact ctatcagagc    3540
ttggttgacg gcaatttcga tgatgcagct tgggcgcagg tcgatgcga cgcaatcgtc    3600 cgatccggag ccgggactgt cgggcgtaca caaatcgccc gcagaagcgc ggccgtctgg    3660
accgatggct gtgtagaagt actcgccgat agtggaaacc gacgccccag cactcgtccg    3720
agggcaaagg aataatcagt actgacaata aaaagattct tgttttcaag aacttgtcat    3780
ttgtatagtt tttttatatt gtagttgttc tattttaatc aaatgttagc gtgatttata    3840
```

```
tttttttcg cctcgacatc atctgcccag atgcgaagtt aagtgcgcag aaagtaatat    3900
catgcgtcaa tcgtatgtga atgctggtcg ctatactgct gtcgattcga tactaacgcc    3960
gccatccaat aacttcgtat aatgtatgct atacgaagtt atgagtggta taacaagacc    4020
tgcaagtgta tggacattta aagtaacagt taattgagaa tacggttgac ctggcatgtt    4080
gttcgaatca atatccaggc acaagtacca ggtgctaaag aaaaagtact ctcatatttg    4140
cttgattgct gcttgggcta ttttaactaa ctactaacaa tattttgctt aaaaaatggt    4200
aaatatgaat gttttacaga aaaataaaaa atgtatatat ataaaatctc gagctagctg    4260
agggttttgg gagcagtcaa agggattcct tatttcttcc aaaaaaaaaa aaacaaccct    4320
tttacttaac atttatcagc tgcatttaat tctcgctgtt ttatgcttga ggactgactg    4380
atactctcat cagctagcga atcatgttga gttttccct ttccgaatgg atcaaccaca    4440
gtagatgcaa attttctggc aggaacccct tggttgaaaa gttcattaat ttcactgaag    4500
gttctaccag ttgtctcagg cagatcgatg atgacccaag ctaaagtgac tgctgtgaaa    4560
ccacccagt atagaccagt tttggcaccc cagttccaat cgctcacgtt tagcatatag    4620
ggcgttaata tagcgttaat aacggccatg agattgtagc aaatacgggc cagcactata    4680
gtcttagttc tcaactccgc tgatggaatt tcagcaacga tacagtaaac aactgcaccg    4740
ataccagcat tgtaaaagaa tgataaagcc agcaataaac caccggcacc attactagcg    4800
ctgcttccag aaccaaaacc cattccacca ataataaata agcagaccat tgaaatgca    4860
agaccatagg tcagtattgt ccatctacca acacggccag atattaccca ggagcaaagt    4920
gtaccgcta acccaagaca gtactgaatt agagaaaaag taaacgcctt gtcggtggcc    4980
ataccgtgctc tttcaaaaaa atatgtcgag taaccaagta aaacggcacc gctactattt    5040
tgagctaccc aagttaaaca tgcaagtctc gttcttcttc cattaactcc cttgaaacaa    5100
ttaaagaatg atcctgattt agatgctaaa agtctttctt tttcaatagt caattcaatc    5160
tgctttaaag taagatcaac ttgaatgtcc ttctcggcgc ctttaccact caaaattctg    5220
cttaaagatt ttcttgcctc agcgacccta tcctttctca ccaaccacca gggcgactca    5280
ggagcgaaaa agataccgat cattaaagga gcaggccaaa tccattgtaa agcaaatggc    5340
aattatagc ccaagtcgga gttccctaaa ttctcttgtg agttttttcat aataccagag    5400
gcgaagattt gaccaaataa ccaacaaatg ttggagtaac tggtcatgta atatcttaat    5460
gctaaagggc aaacttccga agcataagta acagccaaac tttggaaaca accccatggt    5520
atagctgaga gaatttgtcc cacagcaatc atagctaaac ttttacagta gtagaggata    5580
aagatataag cagttaacaa accaagtgct gtaatcatcg tataacgatt ccccataaat    5640
tcaaccatat aagtcgtgat ttgcaaacca atcatctcac cacaaaggac acacatgttt    5700
aaaccaatct gccattggga agtaatttcg taagaaccct ccccgttcaa agtaccgaat    5760
tttctctgaa aaactggcag gcatacagt gcgctcagta gtgcggtatc ataaccttcc    5820
ataaccaggg tagtagacac taatatggac cacagggctg cttttggata ttttagcaac    5880
gcctgcttca aagtcatgct ttttttcctcg ctgttagctt catttgcatc atcagtagcg    5940
ttcatctcat taatcacatt ctcgttatct tcgtcagaat ctcctaactg ggctgaattg    6000
gtggtgaact ctaagtggtc tagctcaaag gcactatcct ttttcccttc ttcaaaatct    6060
tcagtattga aaacctcctg ttggtttaca atatctcttg aagactcaga atgttttta    6120
tcctcatttt ttgaggcagc cttcttcttg cttaccaatg aaatgatatt tttcatatta    6180
```

```
tactattttt ttagttgttt gatgttcttc tatgtagcat cagaaagaaa caccaacccg   6240
aaaattcttc aaacaatcaa taccaaaccg ctttatataa aaaattaaga tgtcgacatt   6300
ccttattttt tactgagttc gttaaagttg ggtacactct tgattactgt aattgtctct   6360
gtatgtccct caagcccggt acgttgtcat tttctagtac gcatcaacgg agtgttacat   6420
gatagataga ccgagtagaa tctatggcta tggggtaatt aaaaccttaa agctcctttc   6480
gctgccatag taatacgaat agaccttggc tatagtaagt tgcatctgta ccgtagagat   6540
tcttgcaact cgcttaaact ctcgctttta gataatattt ctccttattg cgcgcttcgt   6600
tgaaaatttc gctaaacacg gggtttaagt taaagtttac aggatttatc cggaaatttt   6660
cgcggacccc acacaattaa gaattggctc gaagagtgat aacgcatact tttcttttct   6720
ttttttagtt cctagcgtac ctaacgtagg taacatgatt tggatcgtgg gatgatacaa   6780
acaacgtaag atgaatagtt ccttcctcaa ttcttcttgc agcatcattt tcttgaggcg   6840
ctctgggcaa ggtataaaaa gttccattaa tacgtctcta aaaaattaaa tcatccatct   6900
cttaagcagt ttttttgata atctcaaatg tacatcagtc aagcgtaact aaattacata   6960
aatgactatt tctgatcatc cagaaacaga accaaagtgg tggaaagagg ccacaatcta   7020
tcaaatttac ccagcaagtt ttaaagactc caataacgat ggctggggtg atttaaaagg   7080
tatcacttcc aagttgcagt atattaaaga tcttggcgtt gatgctattt gggtttgtcc   7140
gttttatgac tctcctcaac aagatatggg gtatgatata tccaactacg aaaaggtctg   7200
gcccacatat ggtaccaatg aggactgttt tgagctaatt gacaagactc ataagctggg   7260
tatgaaattc atcaccgatt tggttatcaa ccactgttct acagaacacg aatggttcaa   7320
agagagcaga tcctcgaaga ccaatccgaa gcgtgactgg ttcttctgga gacctcctaa   7380
gggttatgac gccgaaggca agccaattcc tccaaacaat tggaaatctt tctttggtgg   7440
ttcagcttgg acttttgatg aaactacaaa tgaattttac ctccgtttgt ttgcgagtcg   7500
tcaagttgac ttgaattggg agaatgaaga ctgcagaagg gcaatctttg aaagtgctgt   7560
tggattttgg ctggaccatg gtgtagatgg ttttagaatc gataccgctg gtttgtattc   7620
gaaacgtcct ggtttaccag attccccaat ttttgacaaa acctcgaaat tacaacatcc   7680
aaattggggg tctcacaatg gtcctaggat tcatgaatat catcaagaac tacacagatt   7740
tatgaaaaac agggtgaaag atggtagaga ataatgaca gtcggtgaag ttgcccatgg   7800
aagtgataat gctttataca ccagtgcagc tagatacgaa gtcagcgaag ttttctcctt   7860
cacgcacgtt gaagttggta cctcgccatt tttccgttat aacatagtgc ccttcacctt   7920
gaaacaatgg aaagaagcca ttgcatcgaa cttttttgttc attaacggta ctgatagttg   7980
ggctaccacc tacatcgaga atcacgatca agcccggtca attacgagat ttgctgacga   8040
ttcgccaaag taccgtaaaa tatctggtaa gctgttaaca ttgctagaat gttcattgac   8100
aggtacgttg tatgtctatc aaggtcagga gataggccag atcaatttca aggaatggcc   8160
tattgaaaag tatgaggacg ttgatgtgaa aaacaactac gagattatca aaaaagttt   8220 tggtaaaaac tcgaaggaaa tgaaggattt ttttaaagga atcgccctac tttctagaga   8280
tcattcgaga actcccatgc catggacgaa agataagccc aatgctggat ttactggccc   8340
agatgttaaa ccttggtttc tcttgaatga atctttcgag caaggaatca atgttgagca   8400
ggaatccaga gatgatgact cagttctcaa ttttggaaa agggccttgc aagccagaaa   8460
gaaatataag gaacttatga tttatggtta cgatttccaa ttcattgatt tagacagtga   8520
ccagatcttt agcttcacta aagagtacga agacaagacg ctgtttgctg ctttaaattt   8580
```

```
cagtggcgaa gaaattgaat tcagcctccc aagagaaggt gcttctttat ctttattct     8640 tggaaattat gatgatactg acgtttcctc cagagttttg aaaccatggg aaggtagaat    8700
ctacctcgtc aaataaaatt agtgccggct tttttttagc gcgtacttta acgaaataac    8760
acatgatttt tcacatgatt tttgttagat aaatttttta tatgtaaatg atgatagcgt    8820
aaaagcactg ttgataattt gtttcaccat tatgggtaaa tgtgttttc tacatgaccc     8880 tcgttcatta tgatatttag cgtgtatata atgtgaatt  ccaaattatt aatgaggcat    8940
aagaagcact atcctttctc ttcggatgaa acaagggag  aagaaacctg tgctggtatt    9000
aatgctgaaa tgtcttgcta agaatcatac aaggtgtgta ttttatttaa taagaaaag     9060 aaaaggacta gatataaaaa gtgaaatgaa tataagatag cgttaagaga tgtccgcagt    9120
acttgacaca taatttagcg ttttctcggg aagctctgtg atttttatgat tcaataacac    9180 agcgtaattg atttcgtgat agttcgatcc tatatg                              9216

<210> SEQ ID NO 3
<211> LENGTH: 3736
<212> TYPE: DNA
<213> ORGANISM: Artificial Sequence
<220> FEATURE:
<223> OTHER INFORMATION: MAL2-8c construct

<400> SEQUENCE: 3
agaactttga ctcttctaca acgtgaatgc ctttgataag aatgaaattc caaaacaagt      60
aatgttggga ggtagatttc ctccactgct aattccaact acgtgtgcat ttttcaatag     120
taatattccg tcacaagagg cttatttca tttttctctac cctcatctttt ttctcacttt    180 tttccttaca atgaatacat gtgatataga tacttaattg tctgtttttgc gagcttgctt    240 cttcatatct atgtaatatg ggccaggtca acccaacatc taccaattat ctatatgaag    300
aaaaatatga ttggtagtta ccgccaatgc atagatttta gacaacttaa taaggccatg    360
ttaaagggtg cattcccact atcgcgctta ggattggatg aagcataact tttcttcact    420
gtcaaattgc atcgtagtta tatcagatcc aaataaaaaa tgaaataac aataacaagc     480 cttctatttt ttcttgtcat gttaaacgg tcatggaaga cctgaactaa agtgttttag     540
taaaccaatt ggagtgagag ttttcattc cgaagattct ttatctcaaa attcttttat     600
cgaaagacac ttctgtgtca ctgtccgttc aatcagtcag atagttccaa ctccgatgtc    660
ttccaatacc tcaacgaaga ccgaaaata aaggttttgt tgacggagt gtgttgatta      720 gtgcattggt gacgtgggt agcaaaatcc agatacttct attttttgaa aaagaaagga    780
gagagtgcta gaatgttttc acgtttatca gtacacgaaa acaaaacct gaagcaaatg     840 attaccataa ctattgtcca cttatgggga agttgctaaa ataacacat tatttactaa     900 gggaacacaa tttgctcata gtatacttga cttttttac ttaacttttg cagcgattgg    960
tgatgaaaat gagcatgcag actaataggt aggaaagtag aactacttag aaacattctc    1020
cttaagtgtt ttcaccacta agcattttat atttaattgt taaaaatat atactattga    1080 agaaccactt tcctgaaata tcaagaacaa aaagtctgc actatggtcc cgcaattgat    1140
gcatttgaga attcttttaa ctcaatagta atatgcattg ttcttatcta aaaaattgca    1200
ggtacctgca gactaatccg ggtcatgatc tgcgctgcgc ccgtcatccc accccgtgct    1260
gcctgccact tgaagctacc ccgggttaa taattcgttc tttaagttct acaacttaaa    1320
tacaggcagc taaaaaactg ggttcgagag ttttccactt tatagacaaa aataaaaata    1380
```

-continued

```
ctgccagaaa atttatcata taataatatg ggtattgcga acagtcttg cgactgctgt      1440
cgcgttcgtc gagtaaagtg tgacaggaat aaaccatgta atcgctgcac tcagcgcaat      1500
ttgaactgca cttatcttca accgttgaaa aagagaggtc caaaatccat tagagcagga      1560
agcttaaaaa aaatagcgga agtgcagatg gtgagtatga ataataatat tatgaccgct      1620
ccggtggtat gtaagaaggt tccgaaaaac ctgattgatc aatgtttgag gttgtatcat      1680
gataacttat atgtaatttg gccaatgctt tcctacgatg atcttcacaa gcttttggag      1740
gaaaattatg aggactgcag cacttattgg tttctggtat cccttttcggc agctactctt     1800
agcgacttgc aaaattgaaat agagtatgag gaaggagtca cttttactgg agagcagtta    1860
tgcactcttt gcatgttatc tcggcaattc tttgacgacc ttagtaacag cgacatattt     1920
cgaatcatga catactattg tttgcaccgt tgttacgcgc agtttgctga tacaagaact     1980
tcatacagac tttcttgtga ggctattggc ctcatcaaga tagctggatt ccatcgggaa     2040
gaaacctatg aattccttcc cttcggtgaa caacaactca aaggaaagt ttactattta     2100
cttcttatga cagagagatt ttacgctgta tatattaagt gtgtcacgag cctagataca   2160
acaatagcgc caccactacc agaggttgta acagaccctc gtctttctct ggaaagcttc    2220
cttgaggtga ttagagtttt cactgtacct ggaaagtgtt tttatgatgc tttggctact    2280
aactgtgtcg atgattcctg caccgaagac tctctaaaaa ggatatggaa cgaacttcat    2340
accacatcac ttgatataga gccatggtct tatggctatg tggacatttc attttctcga    2400
cattggatta gggcgctggc ttggaagcta gtgtttcaga tgaatggtac caagttttc    2460
tcaaacgcca ataatgctca catattggtc gaaattgcaa aggatatgct ggacgacata    2520
ttcttaactc caaacaacct gtatgatgta catggtcctg aataccaat gaaatcattg    2580
gaagtagcca atgcattggt agatatcgta aataagtatg atcacaatat gaagttggag   2640
gcttggaata ttttgtgcga tgtatccaag ttcgttttct ccctgaaaca ttgcaatcat   2700
aaaatgtttc aaaggttttc aactaaatgt cagagtgctc taatcgattt gcctatctct  2760
agaccactgc gcctaaatga tgattccaaa gatgaagacg acataattcc ttaatttatt   2820
gttcacgccg ttcacttata cgagatagat atactgatag agtgtgagtg atattcttaa   2880
gtcttgctttt tcgagggtgt aagaagctat gttcttcagg cgagattatt ctactcctgc  2940
cttacttgtt tgtaatattt agttctgatg gtcatgataa ttctatatac agttacatta   3000
agtatatact taagcgggca gcttactaat ataaattttg tggcattttt gttgggatat    3060
gagaatcatg tatcgttgat ttacaaagcg aatttacgtt accaggaata gggaatactc    3120
tcttgaattc taacataagc acagaaatgc tgaaagaata cgtcaaaaag taaatttaca  3180
gaattaaaaa aaaataatt gttgccggaa catgaataga gtgtatcagt ttaaacgcac    3240
actacttcat aatggtgcaa atttgccctc attacgtgat aacaccactc taactgatgc   3300
tcgtaatgtg ttaaagtact tacaagtgct tggttttcca agcaacaaaa tagcggctgc   3360
ggatactgtt ggaactctta tcatatttag caatcgtgcg gaagctaaca gtaccgctat   3420
gacgaagaca gtgtcatact gttatcgtaa ctacgggcat agttttttact tcactcatta   3480
caaatacgac tattttccta gtgagattag ttatatggca aaacttggcg atgccgccgt   3540
caaccatacg gacttaccct actttaggaa caacaaacgg ctaacaacgc aagaagtcaa   3600
tgccttccaa catccaattg tcgaatttta gtaagtgctc aggtattacg ttatgtacat   3660
gtatgatact tttgattaac atcctttata cacaaagatg tatgcatgaa tggtgcaaat  3720
atctcgacga tgcgca                                                   3736
```

<210> SEQ ID NO 4
<211> LENGTH: 616
<212> TYPE: PRT
<213> ORGANISM: Artificial Sequence
<220> FEATURE:
<223> OTHER INFORMATION: MAL11 product

<400> SEQUENCE: 4

```
Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asp Phe Glu Glu Gly Lys Lys Asp Ser
            35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Val Ile Asn Glu Met Asn Ala
65                  70                  75                  80

Thr Asp Asp Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
            115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
            195                 200                 205

Met Ile Ala Val Gly Gln Ile Leu Ser Ala Ile Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
    275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asn Cys Phe Lys Gly Val Asn Gly Arg Arg
            355                 360                 365
```

-continued

```
Thr Arg Leu Ala Cys Leu Thr Trp Val Ala Gln Asn Ser Ser Gly Ala
    370                 375                 380

Val Leu Leu Gly Tyr Ser Thr Tyr Phe Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
        435                 440                 445

Ile Gly Gly Met Gly Phe Gly Ser Gly Ser Ala Ser Asn Gly Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Ile Asn Ala Ile Leu Thr Pro Tyr Met Leu Asn Val Ser Asp Trp Asn
    515                 520                 525

Trp Gly Ala Lys Thr Gly Leu Tyr Trp Gly Gly Phe Thr Ala Val Thr
530                 535                 540

Leu Ala Trp Val Ile Ile Asp Leu Pro Glu Thr Thr Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Ala Asp Glu Ser Ile Ser Gln Ser Ser Ser Ile Lys Gln Arg
    595                 600                 605

Glu Leu Asn Ala Ala Asp Lys Cys
    610                 615

<210> SEQ ID NO 5
<211> LENGTH: 584
<212> TYPE: PRT
<213> ORGANISM: Artificial Sequence
<220> FEATURE:
<223> OTHER INFORMATION: MAL12 product

<400> SEQUENCE: 5

Met Thr Ile Ser Asp His Pro Glu Thr Glu Pro Lys Trp Trp Lys Glu
1               5                   10                  15

Ala Thr Ile Tyr Gln Ile Tyr Pro Ala Ser Phe Lys Asp Ser Asn Asn
            20                  25                  30

Asp Gly Trp Gly Asp Leu Lys Gly Ile Thr Ser Lys Leu Gln Tyr Ile
        35                  40                  45

Lys Asp Leu Gly Val Asp Ala Ile Trp Val Cys Pro Phe Tyr Asp Ser
    50                  55                  60

Pro Gln Gln Asp Met Gly Tyr Asp Ile Ser Asn Tyr Glu Lys Val Trp
65                  70                  75                  80

Pro Thr Tyr Gly Thr Asn Glu Asp Cys Phe Glu Leu Ile Asp Lys Thr
                85                  90                  95

His Lys Leu Gly Met Lys Phe Ile Thr Asp Leu Val Ile Asn His Cys
            100                 105                 110
```

Ser Thr Glu His Glu Trp Phe Lys Glu Ser Arg Ser Lys Thr Asn
        115                 120                 125

Pro Lys Arg Asp Trp Phe Phe Trp Arg Pro Lys Gly Tyr Asp Ala
130                 135                 140

Glu Gly Lys Pro Ile Pro Pro Asn Asn Trp Lys Ser Phe Phe Gly Gly
145                 150                 155                 160

Ser Ala Trp Thr Phe Asp Glu Thr Thr Asn Glu Phe Tyr Leu Arg Leu
                165                 170                 175

Phe Ala Ser Arg Gln Val Asp Leu Asn Trp Glu Asn Glu Asp Cys Arg
            180                 185                 190

Arg Ala Ile Phe Glu Ser Ala Val Gly Phe Trp Leu Asp His Gly Val
        195                 200                 205

Asp Gly Phe Arg Ile Asp Thr Ala Gly Leu Tyr Ser Lys Arg Pro Gly
    210                 215                 220

Leu Pro Asp Ser Pro Ile Phe Asp Lys Thr Ser Lys Leu Gln His Pro
225                 230                 235                 240

Asn Trp Gly Ser His Asn Gly Pro Arg Ile His Glu Tyr His Gln Glu
                245                 250                 255

Leu His Arg Phe Met Lys Asn Arg Val Lys Asp Gly Arg Glu Ile Met
            260                 265                 270

Thr Val Gly Glu Val Ala His Gly Ser Asp Asn Ala Leu Tyr Thr Ser
        275                 280                 285

Ala Ala Arg Tyr Glu Val Ser Glu Val Phe Ser Phe Thr His Val Glu
    290                 295                 300

Val Gly Thr Ser Pro Phe Phe Arg Tyr Asn Ile Val Pro Phe Thr Leu
305                 310                 315                 320

Lys Gln Trp Lys Glu Ala Ile Ala Ser Asn Phe Leu Phe Ile Asn Gly
                325                 330                 335

Thr Asp Ser Trp Ala Thr Thr Tyr Ile Glu Asn His Asp Gln Ala Arg
            340                 345                 350

Ser Ile Thr Arg Phe Ala Asp Asp Ser Pro Lys Tyr Arg Lys Ile Ser
        355                 360                 365

Gly Lys Leu Leu Thr Leu Leu Glu Cys Ser Leu Thr Gly Thr Leu Tyr
    370                 375                 380

Val Tyr Gln Gly Gln Glu Ile Gly Gln Ile Asn Phe Lys Glu Trp Pro
385                 390                 395                 400

Ile Glu Lys Tyr Glu Asp Val Asp Val Lys Asn Asn Tyr Glu Ile Ile
                405                 410                 415

Lys Lys Ser Phe Gly Lys Asn Ser Lys Glu Met Lys Asp Phe Phe Lys
            420                 425                 430

Gly Ile Ala Leu Leu Ser Arg Asp His Ser Arg Thr Pro Met Pro Trp
        435                 440                 445

Thr Lys Asp Lys Pro Asn Ala Gly Phe Thr Gly Pro Asp Val Lys Pro
    450                 455                 460

Trp Phe Leu Leu Asn Glu Ser Phe Glu Gln Gly Ile Asn Val Glu Gln
465                 470                 475                 480

Glu Ser Arg Asp Asp Asp Ser Val Leu Asn Phe Trp Lys Arg Ala Leu
                485                 490                 495

Gln Ala Arg Lys Lys Tyr Lys Glu Leu Met Ile Tyr Gly Tyr Asp Phe
            500                 505                 510

Gln Phe Ile Asp Leu Asp Ser Asp Gln Ile Phe Ser Phe Thr Lys Glu
        515                 520                 525

```
Tyr Glu Asp Lys Thr Leu Phe Ala Ala Leu Asn Phe Ser Gly Glu Glu
    530                 535                 540

Ile Glu Phe Ser Leu Pro Arg Glu Gly Ala Ser Leu Ser Phe Ile Leu
545                 550                 555                 560

Gly Asn Tyr Asp Asp Thr Asp Val Ser Ser Arg Val Leu Lys Pro Trp
                565                 570                 575

Glu Gly Arg Ile Tyr Leu Val Lys
                580

<210> SEQ ID NO 6
<211> LENGTH: 473
<212> TYPE: PRT
<213> ORGANISM: Artificial Sequence
<220> FEATURE:
<223> OTHER INFORMATION: MAL13 product

<400> SEQUENCE: 6

Met Thr Leu Thr Lys Gln Thr Cys Ala Lys Gln Ala Cys Asp Cys Cys
1               5                   10                  15

Arg Ile Arg Arg Val Lys Cys Asp Gly Lys Arg Pro Cys Ser Ser Cys
                20                  25                  30

Leu Gln Asn Ser Leu Asp Cys Thr Tyr Leu Gln Pro Ser Arg Lys Arg
            35                  40                  45

Gly Pro Lys Ser Ile Arg Leu Arg Ser Leu Lys Arg Ile Ala Glu Val
        50                  55                  60

Gln Arg Glu Ser Gly Pro Asn Thr Ile Ala Thr Ala Pro Val Ile Tyr
65                  70                  75                  80

Lys Arg Val Pro Lys Lys Leu Ile Asp Gln Cys Leu Arg Leu Tyr His
                85                  90                  95

Asp Asn Leu Tyr Val Ile Trp Pro Leu Leu Ser Tyr Asp Asp Leu His
                100                 105                 110

Lys Leu Leu Glu Glu Lys Tyr Asn Asp Asn Tyr Val Tyr Trp Phe Leu
            115                 120                 125

Thr Ala Leu Ser Ala Ala Thr Leu Ser Asp Leu Gln Thr Glu Ile Lys
130                 135                 140

Ser Glu Glu Glu Val Thr Phe Thr Gly Lys Gln Leu Ser Asn Leu Cys
145                 150                 155                 160

Ile Ser Ser Cys Gln Gln Phe Asp Asp Leu Asp Asn Ser Asn Ile Phe
                165                 170                 175

Asn Ile Met Thr Tyr Tyr Cys Leu His Arg Ser Phe Ala Gln Ile Ser
                180                 185                 190

Asn Ala Arg Thr Ser Tyr Arg Leu Cys Cys Glu Ala Val Gly Leu Ile
            195                 200                 205

Thr Val Ala Gly Leu His Arg Glu Glu Thr Tyr Gly Ser Leu Thr Phe
210                 215                 220

Glu Glu Gln Gln Leu Arg Arg Lys Leu Tyr Tyr Leu Leu Met Thr
225                 230                 235                 240

Glu Arg Tyr Tyr Ala Ile Tyr Leu His Cys Ala Thr Ser Leu Asp Ala
                245                 250                 255

Thr Ile Ala Pro Pro Gln Leu Glu Leu Val Thr Asp Pro Gln Leu Ser
                260                 265                 270

Met Asp Ser Phe Leu Glu Met Ile Arg Val Phe Thr Val Pro Gly Lys
            275                 280                 285

Cys Phe Phe Asp Ala Leu Ala Ala Asp Ser Thr Asp Ala Ser Cys Thr
        290                 295                 300
```

-continued

```
Glu Glu Ser Leu Lys Lys Ile Trp Asn Glu Leu His Thr Thr Ser Ser
305                 310                 315                 320

Glu Ile Glu Pro Trp Ser Asn Gly Tyr Ile Asp Ile Ser Phe Ser Arg
                325                 330                 335

His Trp Ile Arg Ile Leu Ala Trp Lys Leu Ala Tyr Gln Met Arg Gly
            340                 345                 350

Ser Asn Phe Ser Leu Asn Ala Asn Asn Gly Gln Ile Pro Ile Glu Ile
        355                 360                 365

Ala Arg Asp Met Leu Ile Asp Thr Tyr Leu Thr Pro Glu Asn Leu Tyr
    370                 375                 380

Asp Val His Gly Pro Gly Val Pro Val Lys Thr Leu Glu Ile Ala Thr
385                 390                 395                 400

Ala Leu Val Asp Ile Val Gly Gln Tyr Asp His Asn Met Lys Leu Glu
            405                 410                 415

Ala Trp Asn Val Leu His Asp Val Cys Lys Phe Ala Phe Ser Leu Asn
            420                 425                 430

His Tyr Asn Asn Asp Met Leu Lys Arg Phe Ser Thr Lys Cys Gln Asn
        435                 440                 445

Ala Leu Ile Thr Leu Pro Ile Ser Lys Pro Leu Gln Leu Asp Gly Tyr
    450                 455                 460

Pro Lys Asp Asn Glu Asp Ile Asp Pro
465                 470
```

MATERIALS AND METHODS FOR CREATING STRAINS OF *Saccharomyces cerevisiae* THAT EXHIBIT AN INCREASED ABILITY TO FERMENT OLIGOSACCHARIDES INTO ETHANOL

PRIORITY CLAIM

This application is a national phase filing of International Application No. PCT/US2019/042605, filed Jul. 19, 2019, which claims priority to U.S. Provisional application No. 62/700,679, filed on Jul. 19, 2018, the content of which are incorporated herein in their entirety by reference.

REFERENCE TO SEQUENCE LISTING

This application contains a Sequence Listing submitted via EFS-wed which is hereby incorporated by reference in its entirety for all purposes. The ASCII copy, created on Jul. 18, 2019, is named XYLO_0002_01_WO_ST25.txt and is 43 KB in size.

FIELD OF THE INVENTION

Aspects of the invention relate to making and using strains of *Saccharomyces cerevisiae* that are capable of efficiently fermenting high maltose syrups into ethanol thereby either eliminating or reducing the need to convert disaccharides and trisaccharides into glucose through the addition of glucoamylase enzymes to yeast feed stocks.

BACKGROUND

Various species of *Saccharomyces* are among the most important industrially grown microorganisms. Long used to leaven bread, produce beer and wine, and as a source of food flavorings and micronutrients, these organisms now play a central role in the production of fuel, facilitating the conversion of sugars to ethanol. A metabolically complex organism, yeast can grow both aerobically and anaerobically as well, if certain nutritional conditions are met. When grown commercially, as in the production of yeast used to support the commercial baking industry, yeasts such as *Saccharomyces cerevisiae* are grown in highly aerated fermentation tanks. The growth of yeast under these conditions is manipulated to favor the production of yeast biomass. One way in which this is accomplished is to schedule the addition of sugars, such as D-glucose, and the rate of oxygen transfer to the yeast to encourage aerobic growth. Various strains of *Saccharomyces* can also be grown under conditions designed to maximize the production of ethanol. Oftentimes, when the object is to maximize the conversion of sugar to ethanol, the level of oxygen in the fermentation vessel is reduced relative to the levels of oxygen used in the vessel during yeast biomass production in order to favor anaerobic growth.

Most strains of *Saccharomyces* prefer growth on D-glucose although many strains are known to grow on other naturally occurring hexoses and even some disaccharides as well. The ability of different species of *Saccharomyces* to grow on different sugars and in the presence of different levels of oxygen accounts for much of its commercial utility including the central role that yeast currently plays in the conversion of plant bio-mass into ethanol for various uses including its use as a fuel.

One of the best-known pathways for the production of ethanol by yeast is the fermentation of 6-carbon sugars (hexoses) into ethanol, especially D-glucose. One widely used feedstock for the production of ethanol is the polysaccharide starch. Starch is a simple polymer consisting of chains of D-glucose. Currently, in the United States at least, starch derived from corn kernels is the preferred feed stock for bio-ethanol production by *Saccharomyces cerevisiae*.

A single kernel of corn is comprised of ~65-80% starch depending on the growing season and the specific corn variety. Starch in its most basic form is a polymer of many glucose molecules linked through glycosidic bonds. This polymer can take on two basic forms. Amylose is primarily a linear glucose polymer that can contain up to 600 glucose molecules (known as DP or degree of polymerization) linked together by $\alpha$-(1,4) linkages. Amylopectin however consists of large highly branched glucose polymers that can range in degree of polymerization from hundreds of thousands to millions of glucose units. Glucose units in amylopectin are linked together by both $\alpha$-(1,4) and $\alpha$-(1,6) linkages with the latter type providing the branching structure. Together, many amylose and amylopectin molecules intertwine into an ordered superstructure known as a starch granule (looks much like a very small onion with concentric layers). A single kernel of corn contains many starch granules consisting of 70-80% amylopectin and 20-30% amylose.

Starch granules serve to store chemical energy for the seed in a very compact and recalcitrant state. This allows for a large amount of energy to be packed into a small space while inhibiting the use of this energy reserve by microbes. In this form, starch is unavailable to the cells of the seed for energy and must therefore be broken down by enzymes into metabolizable molecules (monosaccharide and disaccharide sugars, i.e. glucose and maltose). The initial steps in producing fuel ethanol from corn are designed to achieve the same goal; breakdown of corn starch to usable cellular energy. However, the cellular energy is being used for fermentation by yeast and converted into ethanol.

The process to extract and hydrolyze corn starch in preparation for yeast fermentation starts when corn is received at the ethanol production facility. Corn is received either directly from the farmer or through other intermediaries at the ethanol plant by rail or truck. Each shipment is tested for quality by monitoring percent moisture, percent foreign particles, and the presence of toxins. Each facility has its own corn standards that must be met to accept a certain corn shipment. Corn of low moisture <=20%, low foreign particles, and minimal toxicity enables the most efficient and highest yielding fermentations. However, corn qualities such as percentage starch content, protein content, the amylose to amylopectin ratio, as well as a multitude of other factors drastically affect fermentation yield. These factors vary by region, corn hybrid, weather, farm practices, and other unpredictable variables. It is therefore common to have drastic swings in ethanol plant productivity due to variation in the corn quality from different harvests.

Once corn has been purchased and received, it is either stored on sight or fed directly to a mill. There are two different milling procedures utilized in the United States known as wet milling or dry milling. Over 70% of the 13.3 Billion gallons of fuel ethanol made in the United States in 2012 was made using what is called a dry milling or dry grind process. For this reason, the application includes-dry milling although the invention disclosed herein can be used with feed stocks prepared by virtually any milling process.

The milling process includes forming the corn into fine flour using any number of milling technologies. The most common mill utilized is a hammer mill that disrupts and grinds the corn kernel using sharpened shafts (hammers)

spinning at high speed around a central axis (think enclosed fan). As the hammers spin they grind corn entering from the top of the mill until the corn is ground small enough to pass through a screen of a given size. Screen size dictates the particle size of the flour and influences many downstream processes. As flour particle size rises, the downstream enzymatic hydrolysis of the starch becomes less and less complete ultimately decreasing the amount of sugar available to yeast and the amount of ethanol that can be produced from a given amount of corn. However, creating smaller particle sizes requires more work (energy) as the hammer mill must operate at a higher amperage to breakdown the particles. Smaller particle sizes also increase soluble solids in thin stillage, reducing centrifuge and evaporator efficiency during co-product feed production (Evaporation is an energy intensive process). For these reasons, milling practices vary across ethanol production facilities; on particles with an average screen sizes between 2.5 and 3 mm are utilized.

The ground corn flour is then mixed with water at a certain ratio in a slurry mixer. The ratio of water to corn flour determines the solids level of the final fermentation corn mash. The solids level is an important parameter in fuel ethanol production. This ratio ultimately determines the amount of sugar that is supplied to the yeast and therefore determines the maximum ethanol titer that can be achieved when the material is fermented. Today ethanol producers in the United States typically favor a 32% corn flour mixture (32% Solids) but solids levels can vary between 28 and 34%, depending on facility and season. Fermentations carried out at these solids levels are known as VHG fermentations (for Very High Gravity). The ability to carry out VHG fermentations drastically increases the efficiency of fuel ethanol production but is currently limited to the aforementioned solids levels for several reasons.

In a typical process to produce ethanol from corn the corn flour and water slurry is mixed with an α-amylase enzyme in a slurry mixer. The enzyme/corn/water mixture (mash) is then pumped to a slurry tank where it is heated to ~90° C. to gelatinize the starch for hydrolysis by the α-amylase. The α-amylase is an endoenzyme and thus hydrolyzes glycosidic bonds within the starch granule. This action quickly reduces the viscosity of the mash as it de-polymerizes the starch polymer into shorter chain dextrins. Typically, the mash is held in the slurry tank for ~ 20 minutes and is then sterilized, further gelatinized, and sheared in a jet cooker at 200° C. Jet cooked mash is then pumped into the liquefaction tanks, treated with a second dose of α-amylase, and held at 80-90° C. for two hours to further break down the starch into dextrins. The mash is then cooled to 30-34° C. and pumped into an 800,000 gallon fermentation tank along with yeast, nutrients, and a second enzyme, glucoamylase, to start a process known as SSF (Simultaneous Saccharification and Fermentation). Glucoamylase is an exo-acting β-amylase that liberates glucose from the non-reducing ends of starch polymers and dextrins. Thus, glucoamylase 'spoon feeds' fermentable sugars to the yeast for fermentation to ethanol. The upstream processing required to produce fermentable sugars from starch for yeast fermentation is time and energy intensive.

Most commonly used glucoamylase enzyme technologies are designed to produce glucose from corn starch at a rate consistent with the rate that yeast will ferment glucose, which is preferred by normal yeast for fermentation. This preference is defined in part by the fact that when presented with a mixture of fermentable sugars, strains of *Saccharomyces cerevisiae* used to produce ethanol ferment glucose first and almost exclusively until virtually all the available glucose is fully consumed. Only after virtually all of glucose is completely consumed, will these strains of yeast switch to fermenting other sugars that may be available in the feed stock.

All the glucoamylase enzymes commonly used in the fuel ethanol industry are inhibited to various degrees by the presence of maltose; and maltose is almost always produced to some degree during the breakdown of starch. The accumulation of glucose in the fermenter is also undesirable as it increases the osmolarity of the environment in the fermentation vessel. Most strains of yeast used to produce ethanol are sensitive to the osmolarity of the fermentation environment; high osmolarity can reduce the efficiency of the fermentation and slow or even inhibit the ability to the yeast to produce ethanol. Accordingly, coordinating the rate of glucose production from the breakdown with the rate of glucose consumption by yeast is also necessitated by the need to reduce osmolality of the fermentation environment.

Because the accumulation of high concentrations of glucose in the fermenter broth may lead to stuck fermentations and tremendous yield reductions, traditional fermentation systems limit the rate of starch breakdown to coincide with the rate of yeast glucose fermentation. This limitation reduces the amount of starch that can be broken down and fermented in each 54-hour fermentation and thus limits maximum fermenter yield. Interestingly, maltose, which is also a fermentable sugar that can be produced from corn starch, is half as osmotically stressful to yeast and thus can accumulate to concentrations that are twice the acceptable glucose concentration in a fermenter. Therefore, the rate of starch breakdown can be greatly accelerated by producing the less stressful sugar maltose. Maltose production allows for higher solids to be loaded into a fermenter leading to higher ethanol titers, lower water usage, lower heat usage, and greater margins.

However, maltose fermentation in standard commercial yeast is glucose repressed and thus the efficiency of maltose fermentations is greatly inhibited by the accumulation of even small amounts of glucose in the fermenter using traditional commercial yeast. Thus, glucose repression has prevented the application of high gravity maltose fermentations. Some aspects of the present invention address the apparent difficulties of high gravity maltose fermentations.

SUMMARY OF THE INVENTION

Various strains of *Saccharomyces cerevisiae* are the industry standard strain for commercial production of fuel ethanol from grains such as corn. One widely used strain of *S. cerevisiae* is the commercially available strain Ethanol Red®. This strain has a robust system for utilizing glucose and includes a functional MAL2 locus which enables the strain to ferment maltose. Aspects of the present invention consists of a modified strain of Ethanol Red® in which maltose fermentation has been modestly improved and glucose fermentation rates have increased, thereby improving fermentation of high maltose syrups and maltose/glucose mixtures and furthermore reducing the requirement for exogenous glucoamylase enzyme. DNA sequencing and extensive genomic assembly revealed the MAL1 gene cluster in the Ethanol Red® strain to be significantly different than the MAL1 gene cluster present in many well characterized lab strains (FIG. 1 and SEQ ID NO: 1). Each MAL1 gene cluster is ~ 10 Kb and encodes three genes for maltose import and breakdown. The MAL11 gene encodes a high affinity, broad specificity maltose transporter that can also transport turanose, isomaltose, alpha-methylglucoside, maltotriose, palatinose, panose, trehalose and melezitose. The MAL12 gene encodes a maltase that hydrolyzes maltose producing two glucose molecules. MAL13 encodes a transcriptional activator responsible for inducing MAL11 and MAL12 transcription in the presence of maltose. In wild type industrial and laboratory strains MAL12 and MAL13 require maltose for induction and glucose, even at a very low concentration, represses expression even in the presence of maltose. In one embodiment of the present invention, the Ethanol Red® strain was modified to also contain a functional MAL1 gene cluster which is redundant to some degree with the MAL2 cluster. The gene encoding the Mal2 transcription factor from the laboratory strain CEN.PK (SEQ ID NO: 3) was also incorporated. While this modified version of Ethanol Red® exhibited a modest increase in its ability to ferment maltose, it also exhibited a dramatic and unpredicted effect on how well it consumed glucose under a variety of commercial starch fermentation conditions. There were also robust yield improvements in the production of ethanol compared the Ethanol Red®. Furthermore, and also unexpected, the amount of exogenous glucoamylase required for complete fermentation is significantly less than what is required of other leading industrial strains.

In another embodiment, the integrated MAL1 gene cluster is not identical to SEQ ID NO: 2 but its encoded protein products share 95% similarity with the protein products of MAL11, MAL12 and MAL13 encoded in SEQ ID NO: 2 and shown as SEQ ID NOs: 4-6. Still other embodiments include integration of MAL1 gene cluster (SEQ ID NO: 2) and MAL2-8c gene (SEQ ID NO: 3) into other yeast strains important for ethanol production. In another embodiment, the MAL1 gene cluster and MAL2-8c genes are not integrated into the yeast genome, instead they are expressed and maintained on a plasmid. The plasmid may either be maintained at one copy per cell or as multiple copies per cell. This is dictated by the plasmid type. The plasmid may contain a CEN/ARS sequence allowing replication and faithful transmission to daughter cells. Furthermore, the MAL1 gene cluster and MAL2-8c may be expressed from the same plasmid or two separate plasmids.

A first embodiment includes a recombinant yeast strain, comprising a strain of S. cerevisiae, and an exogenous MAL1 gene cluster; wherein the strain of S. cerevisiae expresses the exogenous MAL1 gene cluster.

A second embodiment includes the recombinant yeast strain according to the first embodiment, wherein the exogenous MAL1 gene cluster is overexpressed.

A third embodiment includes the recombinant yeast strain according to any one of the first and the second embodiments, wherein the exogenous MAL1 gene cluster comprises a MAL11 gene, a MAL12 gene, and/or MAL13 gene.

A fourth embodiment includes the recombinant yeast strain according to any one of the first to the third embodiments, wherein the MAL11 gene encodes at least one agent that is involved in sugar transport; wherein the MAL12 gene encodes at least one agent that hydrolyzes maltose; and/or wherein the MAL13 gene encodes at least one agent that induces transcription of MAL11 and MAL12.

A fifth embodiment includes the recombinant yeast strain according to the fourth embodiment, wherein the at least one agent that is involved in sugar transport comprises at least one agent that transports maltose, turanose, isomaltose, alpha-methylglucoside, maltotriose, palatinose, panose, trehalose, melezitose, or any combination thereof.

A sixth embodiment includes the recombinant yeast strain according to any one of the first to the fifth embodiments, further comprising an exogenous MAL2-8c gene.

A seventh embodiment includes the recombinant yeast strain according to any one of the first to the sixth embodiments, wherein the exogenous MAL2-8c gene is overexpressed.

An eighth embodiment includes the recombinant yeast strain according to any one of the first to the seventh embodiments, wherein the recombinant strain expresses the MAL1 gene cluster and the MAL2-8c gene derived from a CEN.PK yeast strain.

A ninth embodiment includes the recombinant yeast strain according to any one of the first to the eighth embodiments, wherein the MAL1 gene cluster is integrated into the genome of the strain of S. cerevisiae.

A tenth embodiment includes the recombinant yeast strain according to any one of the first to the ninth embodiments, wherein the MAL1 gene cluster is inserted into the genome of the strain of S. cerevisiae in the subtelomeric region of chromosome VII.

An eleventh embodiment includes the recombinant yeast strain according to any one of the first to the tenth embodiments, wherein the MAL2-8c gene is integrated into the genome of the strain of S. cerevisiae.

A twelfth embodiment includes the recombinant yeast strain according to any one of the first to the eleventh embodiment, wherein the MAL2-8c gene is inserted into the genome of the strain of S. cerevisiae within a region encoding the Dubious Open Reading Frame YEL028W.

A thirteenth embodiment includes the recombinant yeast strain according to any one of the first to the twelfth embodiments, wherein the strain of S. cerevisiae is haploid, diploid, or has a ploidy number greater than two.

A fourteenth embodiment includes the recombinant yeast strain according to any one of the first to the thirteenth embodiments, wherein the MAL1 gene cluster comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, and/or 100% homology to SEQ ID NO: 2 and the MAL2-8c gene cluster comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, and/or 100% homology SEQ ID NO: 3.

A fifteenth embodiment includes the recombinant yeast strain according to any one of the first to the fourteenth embodiments, wherein the MAL1 gene cluster comprises a sequence having at least 85 percent homology to SEQ ID NO: 2 and the MAL2-8c gene cluster comprises a sequence having at least 85 percent homology SEQ ID NO: 3.

A sixteenth embodiment includes the recombinant yeast strain according to any one of the first to the fifteenth embodiments, wherein the MAL1 gene cluster comprises a sequence having at least 90 percent identity to SEQ ID NO: 2 and the MAL2-8c gene cluster comprises a sequence having at least 90 percent identity to SEQ ID NO: 3.

A seventeenth embodiment includes the recombinant yeast strain according to any one of the first to the sixteenth embodiments, wherein the MAL1 gene cluster comprises a sequence having at least 95 percent homology to SEQ ID NO: 2 and the MAL2-8c gene cluster comprises a sequence having at least 95 percent homology to SEQ ID NO: 3.

An eighteenth embodiment includes the recombinant yeast strain according to any one of the first to the seventeenth embodiments, wherein the MAL1 gene cluster comprises a sequence having at least 95 percent identity to SEQ ID NO: 2 and the MAL2-8c gene cluster comprises a sequence having at least 95 percent identity SEQ ID NO: 3.

A nineteenth embodiment includes the recombinant yeast strain according to any one of the first to the eighteenth embodiments, wherein the MAL1 gene cluster comprises a sequence having SEQ ID NO: 2 and the MAL2-8c gene cluster comprises a sequence having SEQ ID NO: 3.

A twentieth embodiment includes a vector comprising a MAL1 gene cluster that comprises a sequence having 80%, 81%, 82%, 83%, 84%, 85%, 86%, 87%, 88%, 89%, 90%, 91%, 92%, 93%, 94%, 95%, 96%, 97%, 98%, 99%, and/or 100% homology or identity to SEQ ID NO: 2.

A twenty first embodiment includes the vector according to the twentieth embodiment, further comprising a MAL2-8c gene cluster that comprises a sequence having 80%, 81%, 82%, 83%, 84%, 85%, 86%, 87%, 88%, 89%, 90%, 91%, 92%, 93%, 94%, 95%, 96%, 97%, 98%, 99%, and/or 100% homology or identity to SEQ ID NO: 3.

A twenty second embodiment includes the vector according to any one of the twentieth and the twenty first embodiments, wherein the MAL1 gene cluster and/or a MAL2-8c gene cluster are maintained and expressed in a haploid, diploid, or polyploid of the strain of *S. cerevisiae*.

A twenty third embodiment includes the vector according to any one of the twentieth to the twenty second embodiments, wherein the vector is expressed in the strain of *S. cerevisiae* as a single copy or multiple copies. Consistent with these embodiments, the vector and/or plasmid may either be maintained at one copy per cell or as multiple copies per cell.

A twenty fourth embodiment includes a vector comprising a MAL2-8c gene cluster that comprises a sequence having 80%, 81%, 82%, 83%, 84%, 85%, 86%, 87%, 88%, 89%, 90%, 91%, 92%, 93%, 94%, 95%, 96%, 97%, 98%, 99%, and/or 100% homology or identity to SEQ ID NO: 3.

A twenty fifth embodiment includes the vector according to the twenty fourth embodiment, wherein the MAL2-8c gene cluster is maintained and expressed in a haploid, diploid, or polyploid of the strain of *S. cerevisiae*.

A twenty sixth embodiment includes the vector according to any one of the twenty fourth and the twenty fifth embodiments, wherein the vector is expressed in the strain of *S. cerevisiae* as a single copy or multiple copies.

A twenty seventh embodiment includes a method of producing a recombinant yeast strain, comprising: integrating the exogenous MAL1 gene cluster and/or the exogenous MAL2-8c gene according to any one of the first to the nineteenth embodiments into the genome of the strain of *S. cerevisiae*.

A twenty eighth embodiment includes the recombinant yeast strain according to any one of the first to the nineteenth embodiments, wherein the recombinant yeast strain is made using genetic engineering or wherein the recombinant yeast strain is genetically modified.

A twenty ninth embodiment includes any one of the first to the twenty eighth embodiments, wherein the recombinant yeast strain is capable of fermenting maltose as well as disaccharides and trisaccharides comprised of glucose while simultaneously improving the efficiency and speed of glucose fermentation.

DETAILED DESCRIPTION OF THE INVENTION

Figure 1:
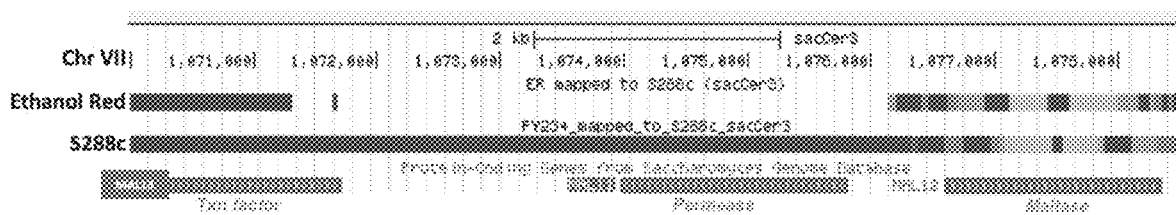
FIG. 1. A schematic drawing illustrating DNA sequence analysis of Fermentis Ethanol Red® strain and alignment of sequencing reads with the MAL1 gene cluster of S288c.

For the purposes of promoting an understanding of the principles of the novel technology, reference will now be made to the preferred embodiments thereof, and special language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

As used herein, unless specified otherwise, the term 'about' means plus or minus 20 percent, for example, about 1.0 encompasses the range 0.8 to 1.2.

Unless specifically referred to otherwise, genes are referred to using the nomenclature suggested by Demerec et al., *A proposal for a uniform nomenclature in bacterial genetics*. J. GEN. MICROBIOL (1968) 50, 1-14.

A "vector" is any nucleic acid molecule for the cloning of and/or transfer of a nucleic acid into a cell. A vector may be a replicon to which another nucleotide sequence may be attached to allow for replication of the attached nucleotide sequence.

A "recombinant" vector refers to a viral or non-viral vector that comprises one or more exogenous nucleotide sequences (i.e., trans genes), e.g., two, three, four, five or more exogenous nucleotide sequences. An "expression" vector refers to a viral or non-viral vector that is designed to express a product encoded by an exogenous nucleotide sequence inserted into the vector.

The term "exogenous" with respect to a polynucleotide means a polynucleotide that is not native to the cell in which it is located or, alternatively, a polynucleotide which is normally found in the cell but is in a different location or is expressing different copy number than normal (e.g., in a vector or in a different location in the genome).

The term "recombinant organism" refers to any organism including, but is not limited to, a strain or a part of yeast whose genetic material has been altered using genetic engineering techniques. In any one of the embodiments disclosed herein, the polynucleotide can be inserted into a cell of an organism including, but is not limited to, a strain or a part of yeast by genetic engineering (e.g., insertion of an expression vector).

The term "express" or "expression" of a polynucleotide coding sequence means that the sequence is transcribed, and optionally, translated. Typically, according to the present invention, expression of a coding sequence of the invention will result in production of the polypeptide of the invention. The entire expressed polypeptide or fragment can also function in intact cells without purification.

As used herein, the terms "protein" and "polypeptide" can be interchangeably used and can encompass both peptides and proteins, unless specifically indicated otherwise.

For those skilled in the art, protein sequence similarity is calculated by alignment of two protein sequences. Commonly used pairwise alignment tools include COBALT (Papadopoulos and Agarwala, 2007), EMBOSS Needle (Needleman and Wunsch, 1970) and EMBOSS Stretcher (Myers and Miller, 1988). The percentage of identity represents the total fraction of amino acids that are identical along the length of each protein. Similarity is calculated based on the percentage of amino acids with similar character over the reported aligned region. Amino acids are considered similar if they share common chemical properties that impart similar qualities to the structure and activity of the entire protein.

Figure 2:
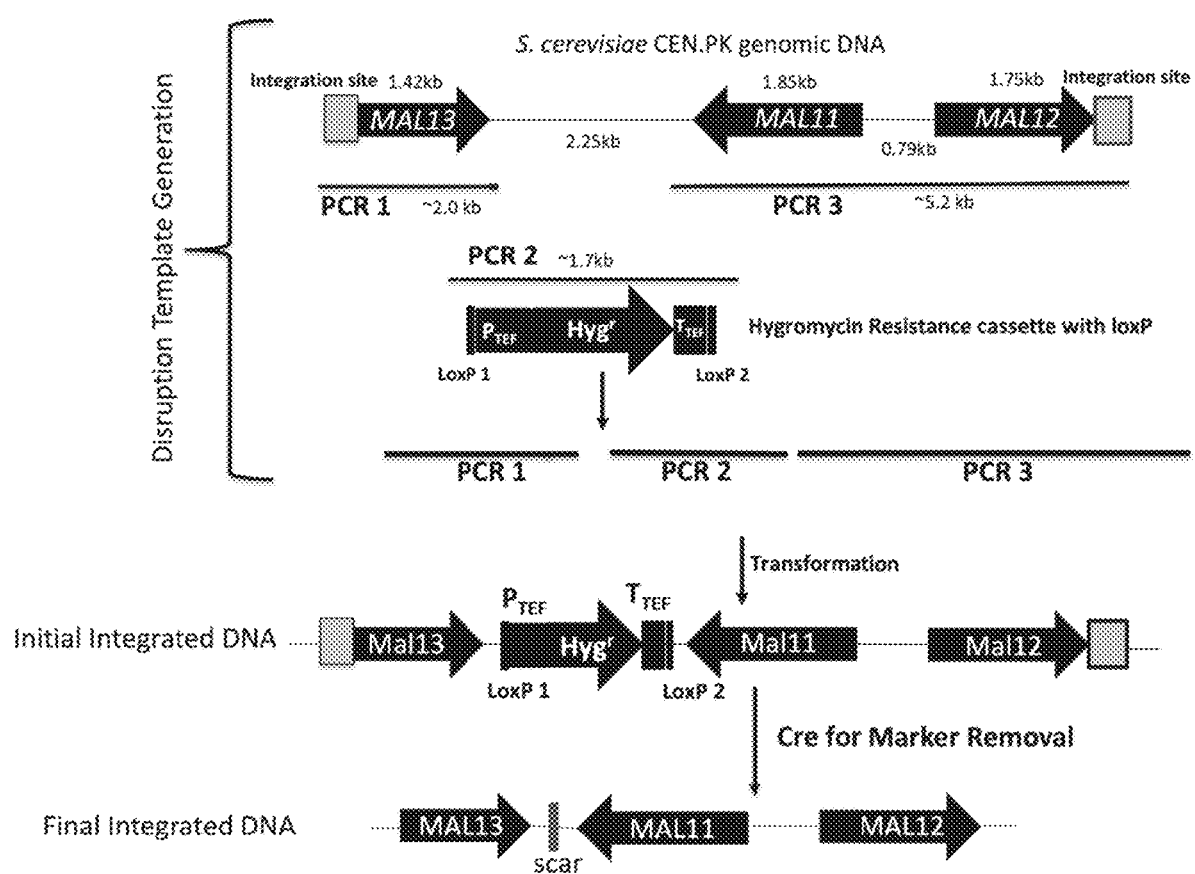
FIG. 2. A schematic drawing illustrating strategy to replace the endogenous MAL1 gene cluster in Fermentis Ethanol Red® strain with MAL1 gene cluster from Cen.PK 113-7D strain.

The endogenous MAL1 locus was modified using direct transformation with three overlapping PCR fragments (FIG. 2). PCR product numbers one and three were generated from genomic DNA template of strain CEN.PK 113-7D. PCR product number two was generated using a yeast expression vector pKC2 as template to amplify a hygromycin resistance gene flanked by LoxP sites allowing for removal by CRE Recombinase. After confirming integration of PCR products, the hygromycin resistance gene was removed, leaving a strain with a small DNA scar and no antibiotic resistance or other foreign genes (FIG. 2). Detailed sequence information is shown in the Sequence Listing section below.

Figure 3:
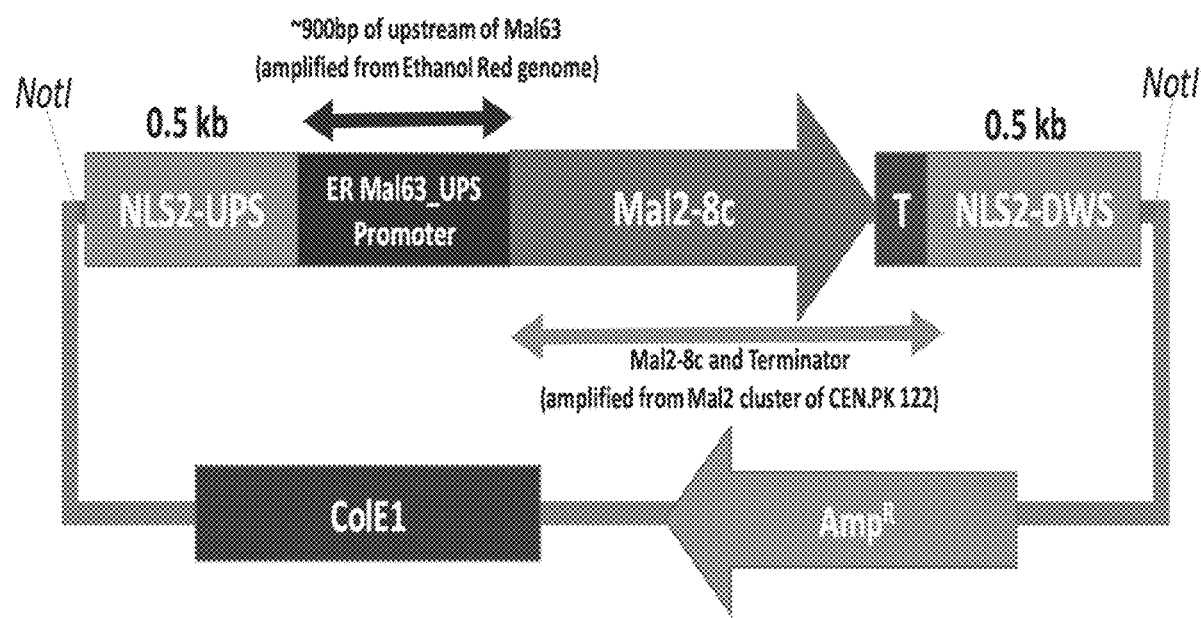
FIG. 3. A schematic drawing illustrating construction of the MAL2-8c gene cassette using overlapping PCR fragments in the pDNLS2 vector targeting Neutral Landing Site 2 as the site of integration.

The MAL2-8c gene with its native terminator from *S. cerevisiae* CEN.PK 122 and promoter region from *S. cerevisiae* strain Fermentis Ethanol Red® strain (for details see Sequence list, MAL2-8c construct) were PCR amplified from the genomic DNA of the respective strains using Q5 PCR reaction mixture (New England Biolabs). The overlapping PCR fragments were gel purified and then cloned into Pmel linearized target vector backbone of pDNLS2 (FIG. 3) using HiFi DNA assembly kit as recommended in the manufacturer's protocol (New England Biolabs). The correct vector assembly with desired genetic components was verified by PCR and sequencing. The DNA of verified MAL2-8c gene cassette was digested with NotI restriction enzyme and gel purified as linear DNA fragments for integration into the designated Neutral Landing Site 2 of selected *S. cerevisiae* strains using CRISPR technology. The linear DNA fragment of MAL2-8c cassette and plasmid DNA expressing both the nuclease and NLS2-targeting SgRNA were transformed into *S. cerevisiae* according to a previously published protocol (Gictz et al., *Yeast transformation by the LiAc/SS Carrier DNA/PEG method*, METHODS MOL BIOL 2006, 313:107-120). The transformed cells were plated on selective YPD media plates supplemented with 50 µg/ml of G418 antibiotic. Plates were incubated at 30° C. for 2-3 days, until colonies became visible. Upon appearance of visible colonies on YPD plates, integration of MAL2-8c gene cassette at the NLS2 site was confirmed via direct colony PCR prior to long term storage in 15% glycerol at −80° C. The resulting strain is known to us as ER-19-11-4.

Figure 4:
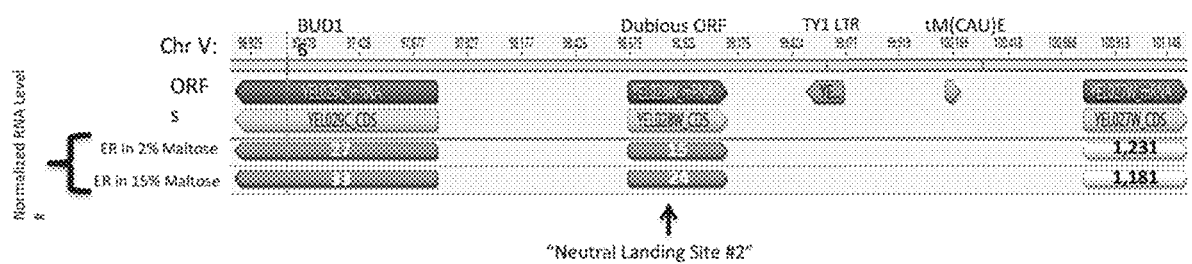
FIG. 4. A schematic drawing illustrating details of the genomic features and gene expression profiles around dubious ORF YEL028W, termed "Neutral Landing Site #2", the site of MAL2-8c integration. YEL028W is a dubious Open reading frame whose transcript does not code for a functional protein. Gene expression values are shown. These values represent transcripts per million, a normalized method of measuring gene expression via RNA-Seq.

Neutral Landing Site 2 (NLS2) was selected as the site of MAL2-8c integration for several regions. First, to avoid disrupting any important genetic elements; a spot-on chromosome V overlapping the dubious open reading frame YEL028W but sufficiently distant from other annotated genes was chosen. Genome-wide RNA expressions were measured in Fermentis Ethanol Red® fermenting either maltose or glucose at both high (15%) and low (2%) concentrations. Under all conditions tested the genes neighboring NLS2 are expressed at moderate levels indicating that this is a region amenable to Pol II transcription under a wide variety of conditions (FIG. 4). Together the analyses disclosed herein indicate the region overlapping YEL028W provides a suitable and stable platform where superior genetic traits can be engineered in Ethanol Red® and their derivative strains.

EXPERIMENTAL

Figure 5A:
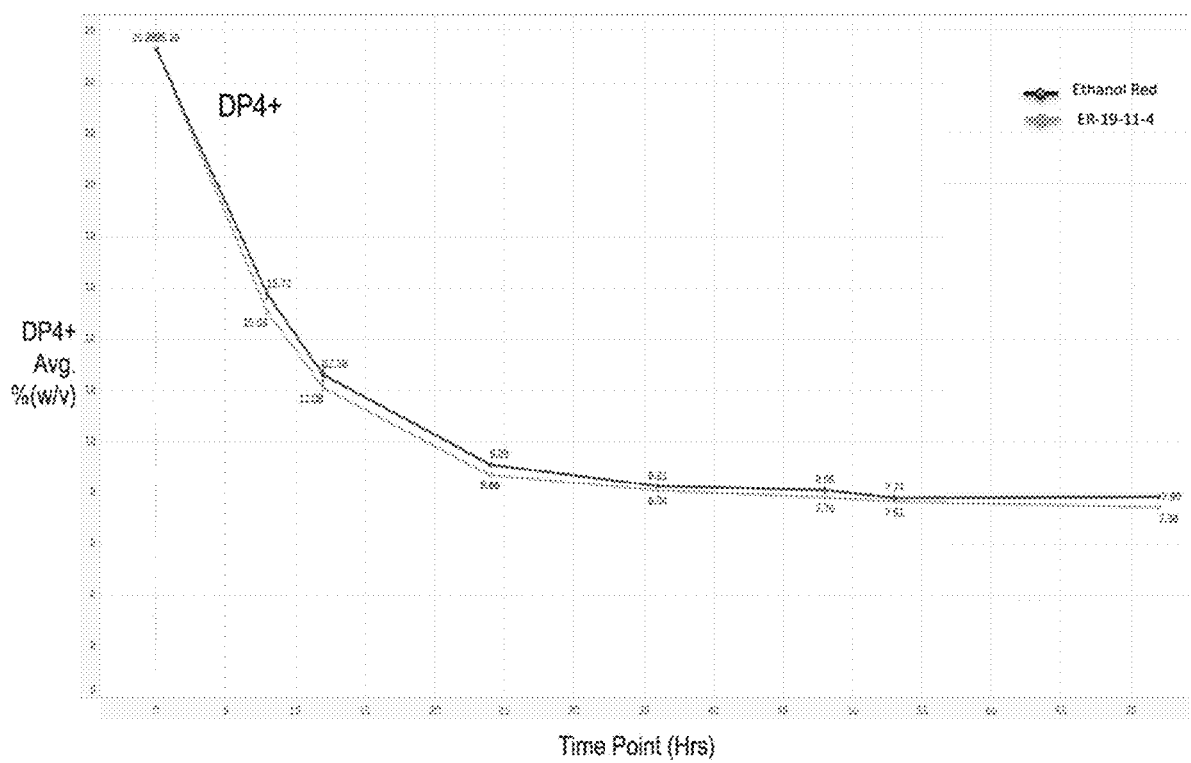
FIG. 5A. A graph illustrating the changes in DP4+ levels from wild type and the maltophilic strain under conditions of maltose and glucose co-fermentation when corn mash is treated with a 1% solution of maltogenic alpha amylase, SEBStar MA.
Figure 5B:
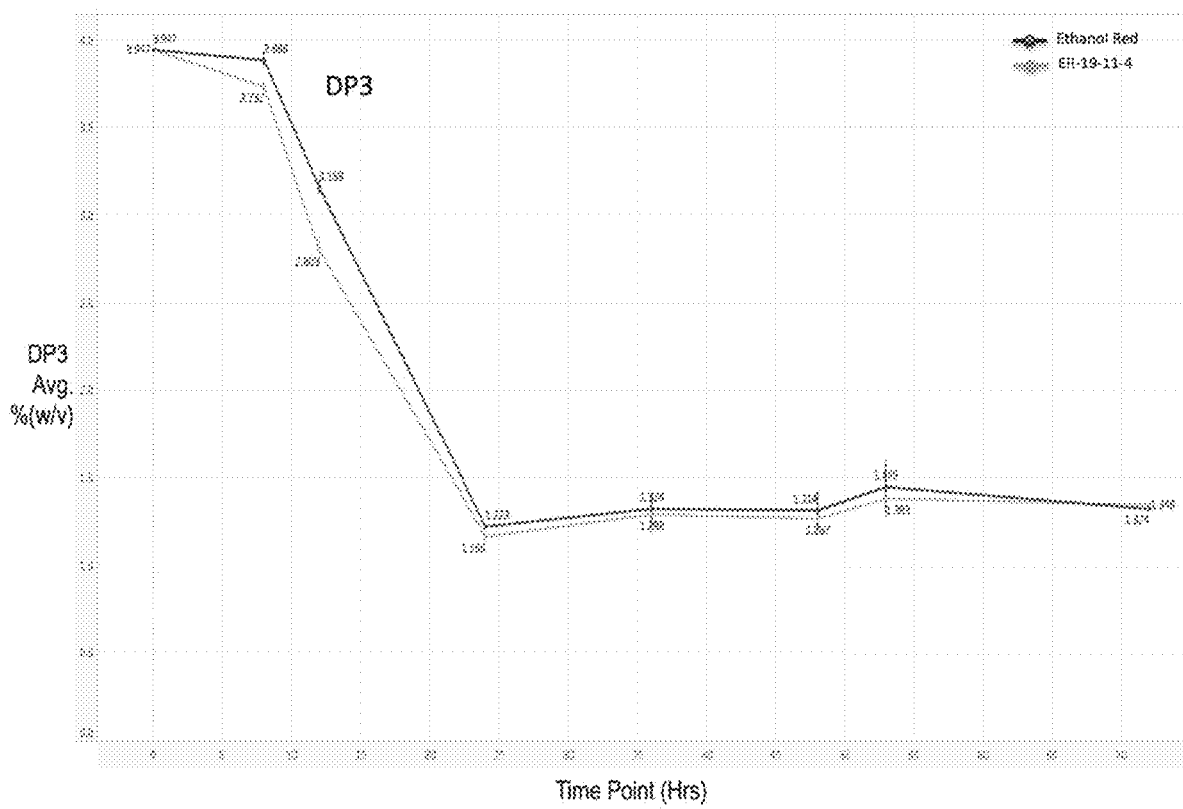
FIG. 5B. A graph illustrating the changes in DP3 levels from wild type and the maltophilic strain under conditions of maltose and glucose co-fermentation when corn mash is treated with a 1% solution of maltogenic alpha amylase, SEBStar MA.
Figure 5C:
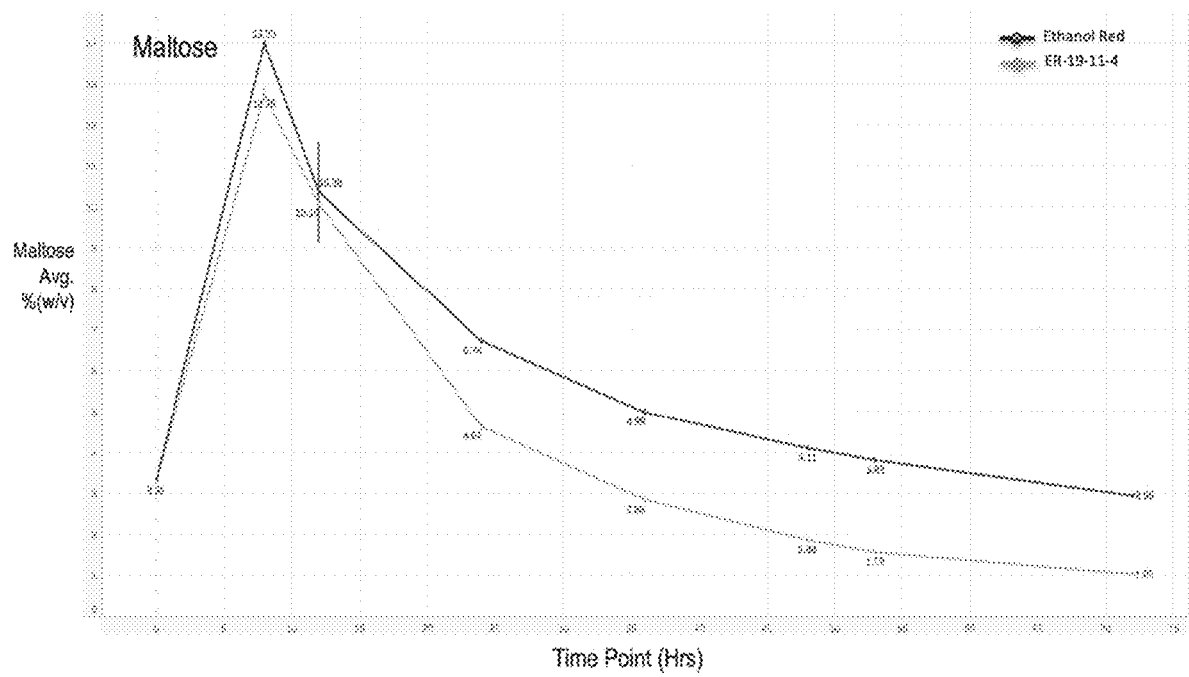
FIG. 5C. A graph illustrating the changes in maltose levels from wild type and the maltophilic strain under conditions of maltose and glucose co-fermentation when corn mash is treated with a 1% solution of maltogenic alpha amylase, SEBStar MA.
Figure 5D:
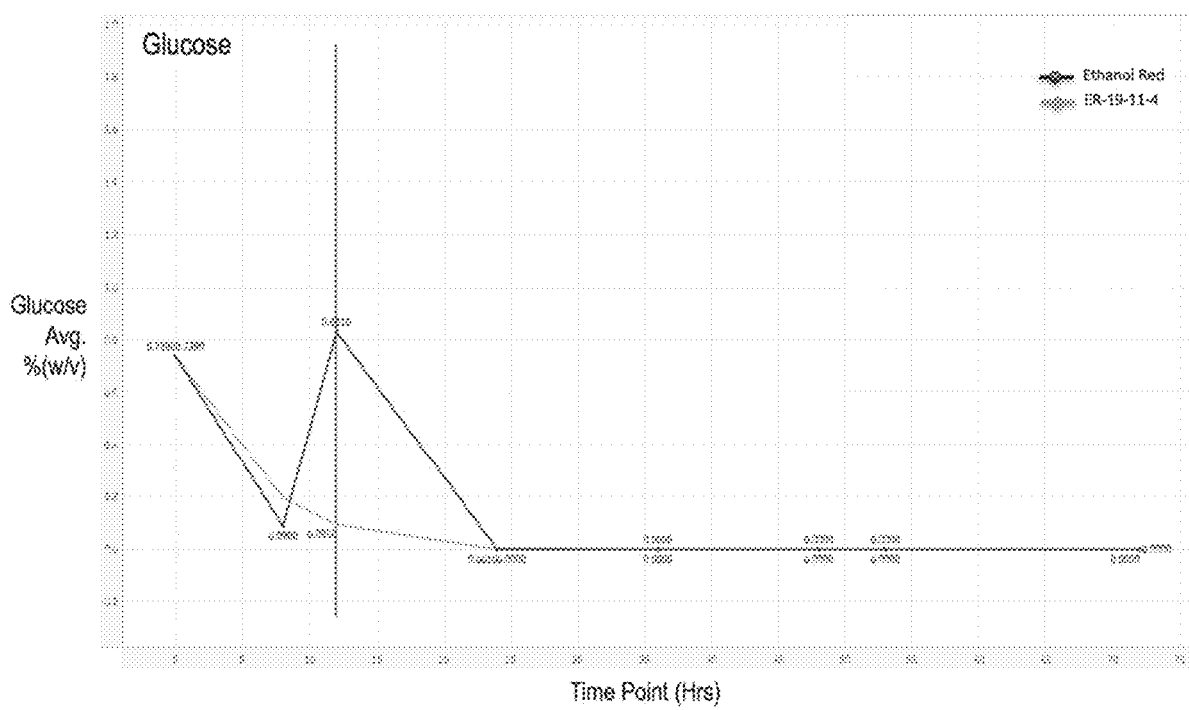
FIG. 5D. A graph illustrating the changes in glucose levels from wild type and the maltophilic strain under conditions of maltose and glucose co-fermentation when corn mash is treated with a 1% solution of maltogenic alpha amylase, SEBStar MA.
Figure 5E:
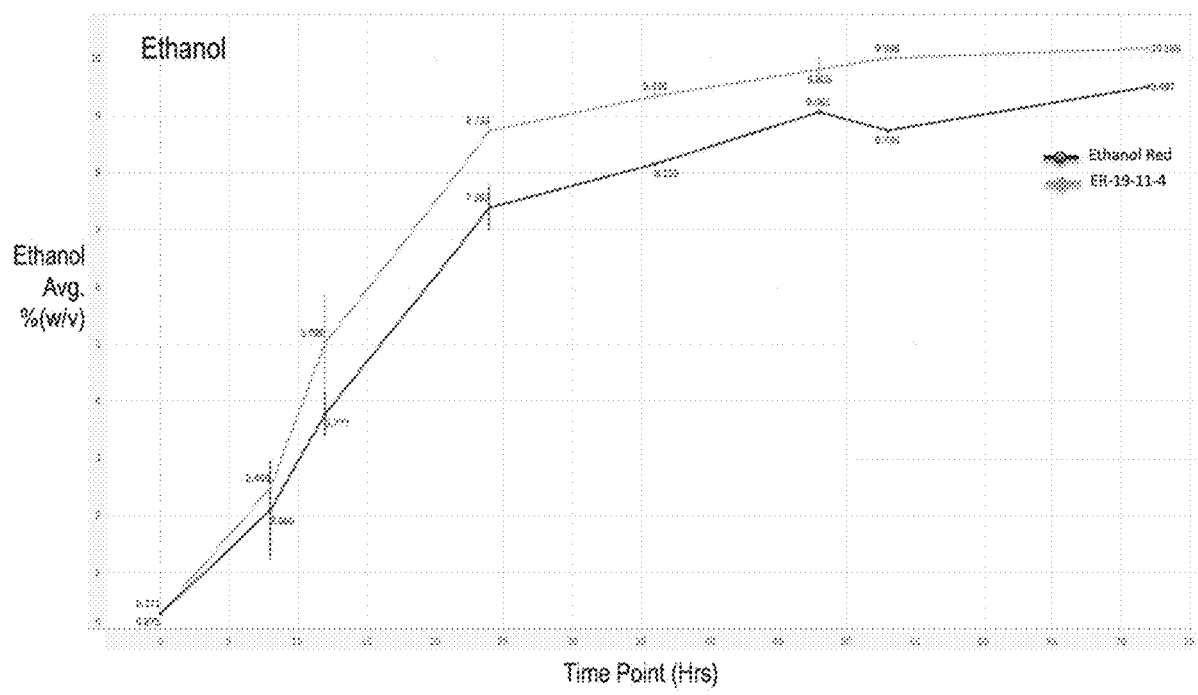
FIG. 5E. A graph illustrating the changes in ethanol levels from wild type and the maltophilic strain under conditions of maltose and glucose co-fermentation when corn mash is treated with a 1% solution of maltogenic alpha amylase, SEBStar MA.

To test the fermentation ability of ER-19-11-4, corn mash containing 31.3% solids was treated with a 1% solution of maltogenic alpha amylase SEBStar MA (Specialty Enzymes). Maltogenic strain ER-19-11-4 produced more ethanol than Fermentis Ethanol Red® at all time points, including fermentation finish (FIG. 5F). Higher ethanol production by ER-19-11-4 is due primarily to increased maltose consumption (FIG. 5C). ER-19-11-4 finished fermentation with only 1.05% (w/v) maltose remaining while the unmodified Ethanol Red® strain left 2.45% (w/v) maltose at the end of fermentation. Both strains finished with equivalent levels of DP3 sugars but the maltophilic yeast ER-19-11-4 consumed DP3 quicker than Ethanol Red®, up until 24 hours when both fermentations reached a steady state (FIG. 5B).

Figure 6A:
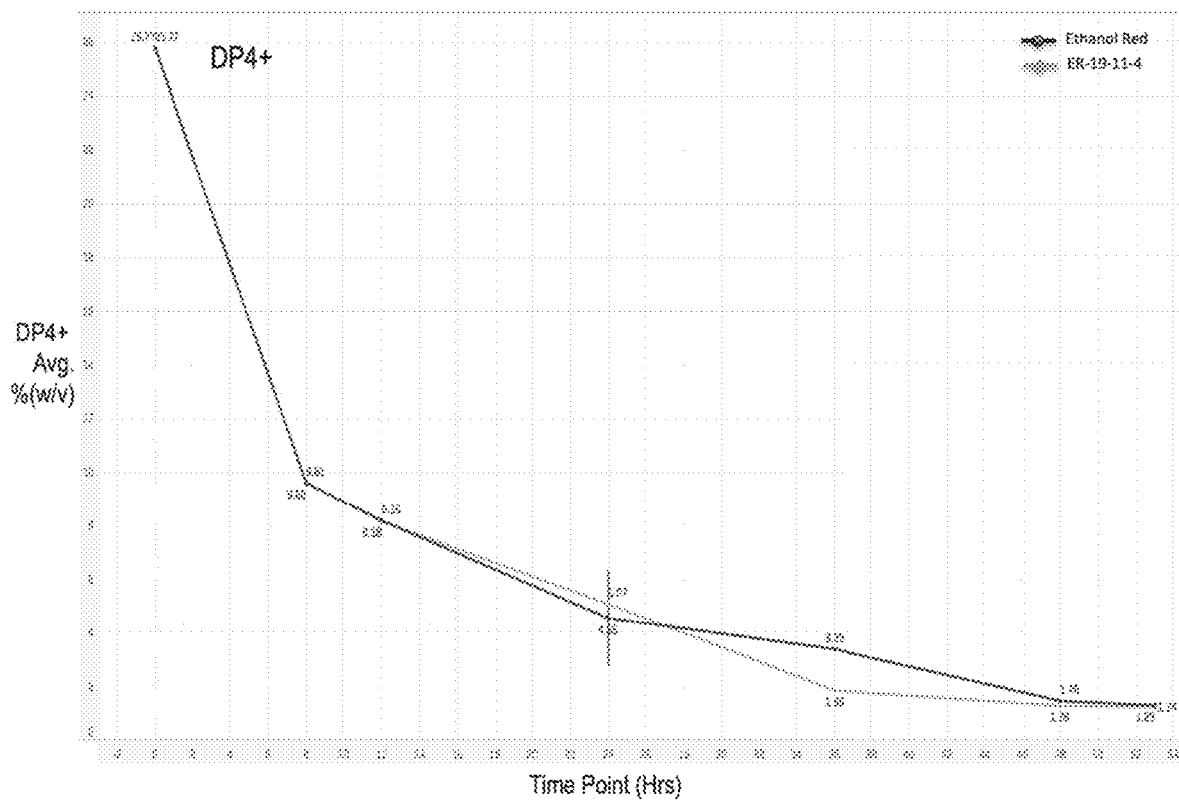
FIG. 6A. A graph illustrating the changes in DP4+ levels from wild type and the maltophilic strain under conditions of maltose and glucose co-fermentation when corn mash is treated with SEBStar MA (1%) and a low level (0.015% w/w) of CTE Global Glucoamylase.
Figure 6B:
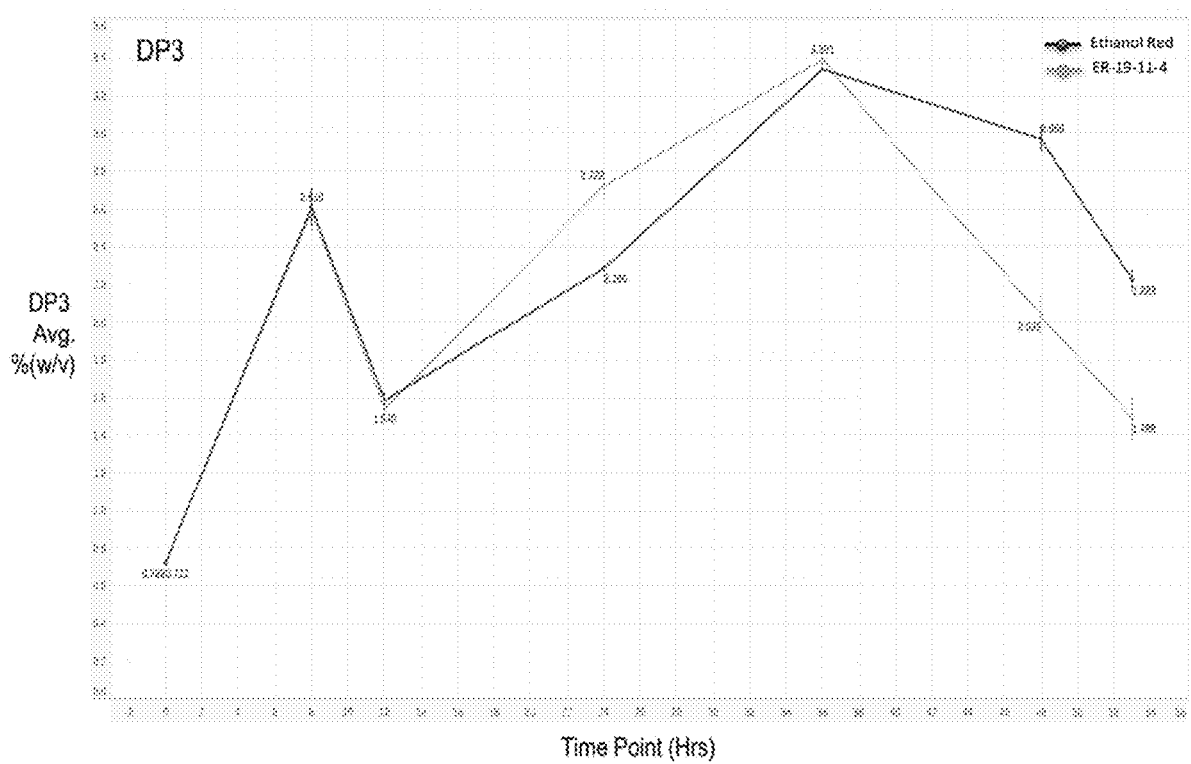
FIG. 6B. A graph illustrating the changes in DP3 levels from wild type and the maltophilic strain under conditions of maltose and glucose co-fermentation when corn mash is treated with SEBStar MA (1%) and a low level (0.015% w/w) of CTE Global Glucoamylase.
Figure 6C:
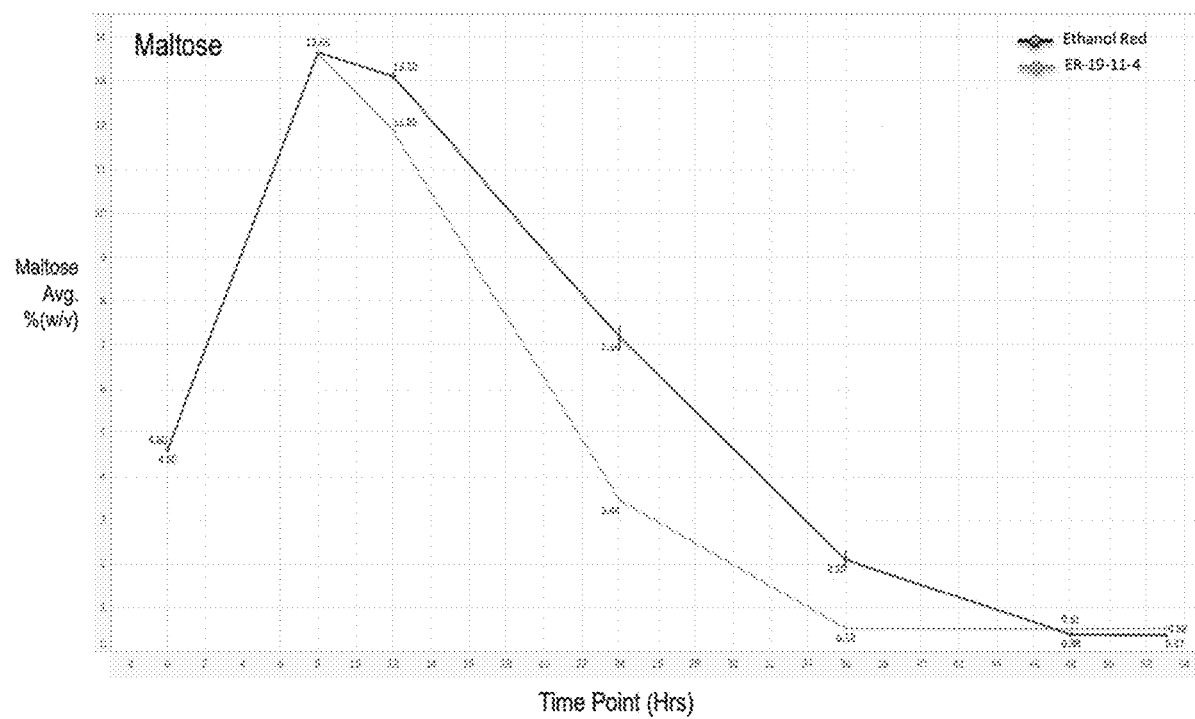
FIG. 6C. A graph illustrating the changes in maltose levels from wild type and the maltophilic strain under conditions of maltose and glucose co-fermentation when corn mash is treated with SEBStar MA (1%) and a low level (0.015% w/w) of CTE Global Glucoamylase.
Figure 6D:
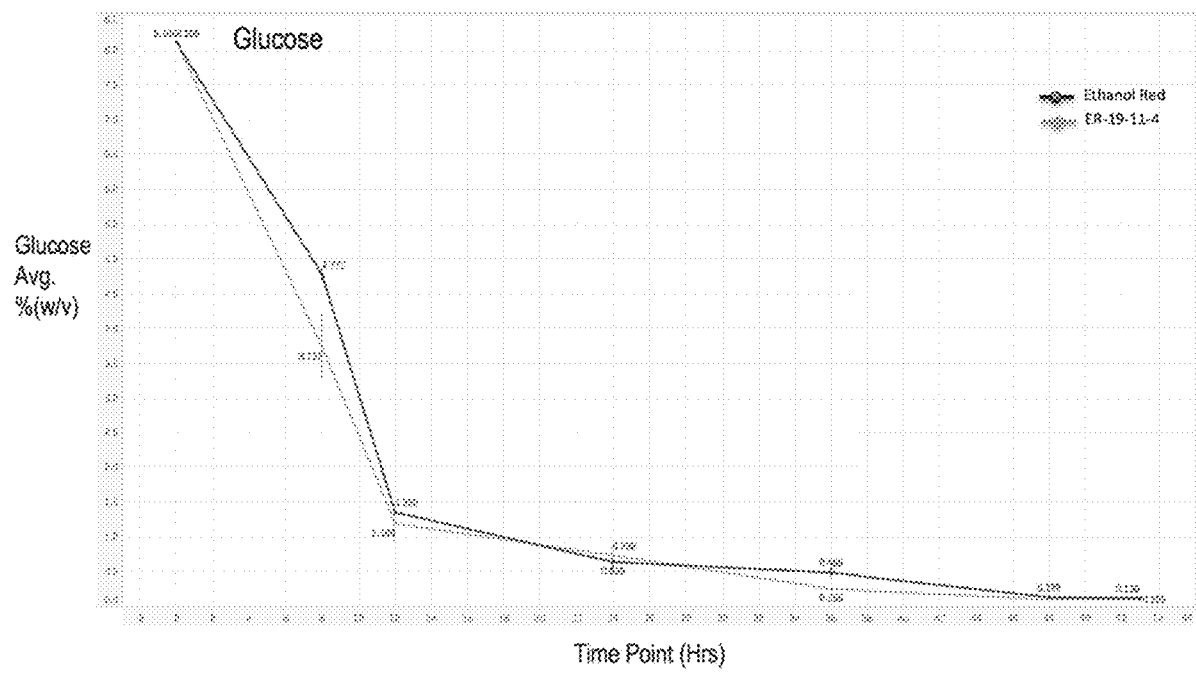
FIG. 6D. A graph illustrating the changes in glucose levels from wild type and the maltophilic strain under conditions of maltose and glucose co-fermentation when corn mash is treated with SEBStar MA (1%) and a low level (0.015% w/w) of CTE Global Glucoamylase.
Figure 6E:
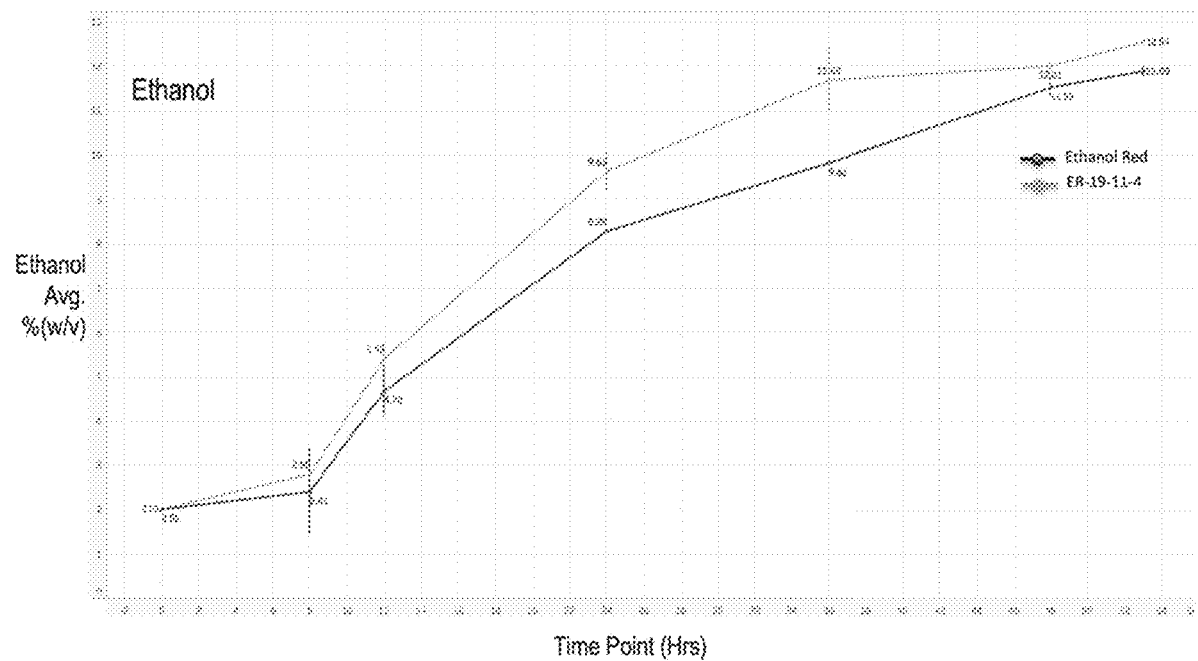
FIG. 6E. A graph illustrating the changes in ethanol levels from wild type and the maltophilic strain under conditions of maltose and glucose co-fermentation when corn mash is treated with SEBStar MA (1%) and a low level (0.015% w/w) of CTE Global Glucoamylase.

As a second test, corn mash with 31.3% solids was treated with 1% SEBStar MA and a low level (0.015% w/w) of CTE Global Glucoamylase. The combined enzyme treatment resulted in more DP4+ breakdown, higher glucose levels, higher final ethanol levels while still producing high maltose syrups (FIGS. 6A-E). Under these conditions, maltophilic yeast ER-19-11-4 consumed maltose faster and produced more ethanol than an isogenic wild type strain (FIG. 6E). ER-19-11-4 also showed slightly improved glucose consumption (FIG. 6F). Combining maltogenic alpha amylase and glucoamylase resulted in more DP3 fluctuation than maltogenic alpha alone; however, after 36 hours the ER-19-11-4 strain consumed more DP3 sugars than Ethanol Red® and final DP3 values at 54 hours were significantly lower in the ER-19-11-4 fermentations (1.5%) compared to Ethanol Red® fermentations (2.2%) (FIG. 6B).

Figure 7A:
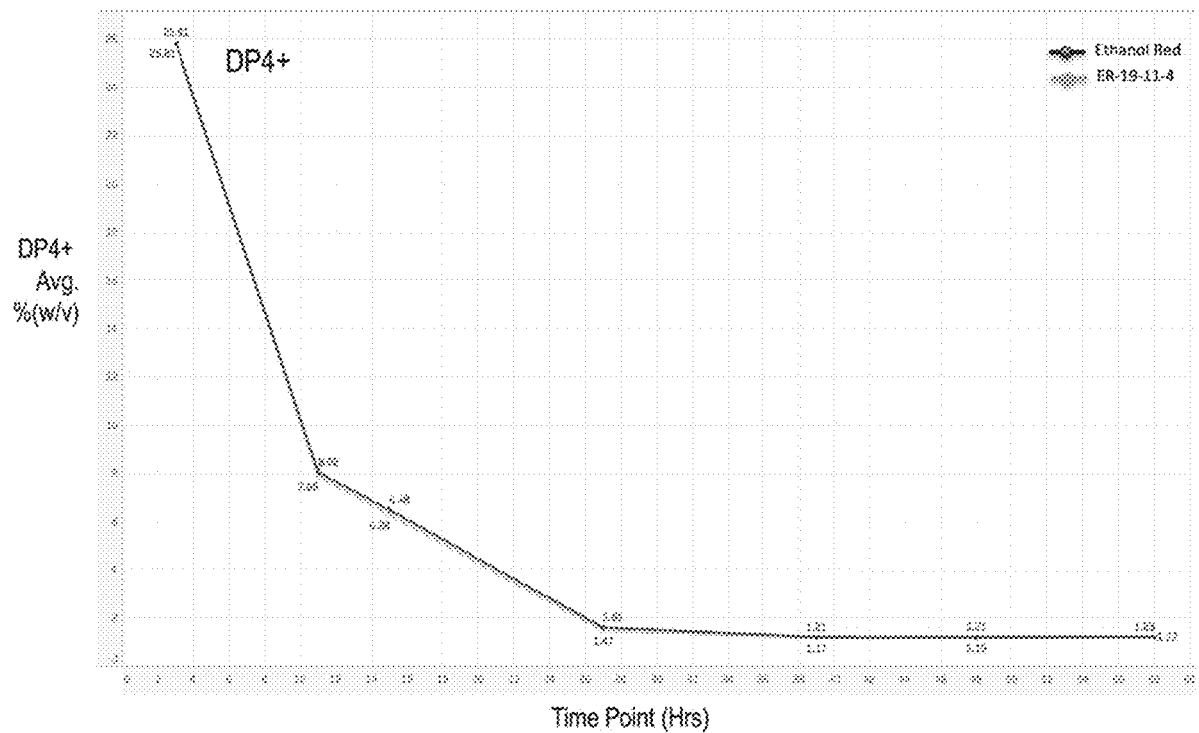
FIG. 7A. A graph illustrating the changes in DP4+ levels from wild type and the maltophilic strain under conditions of maltose and glucose co-fermentation when corn mash is treated with Spirizyme Achieve Glucoamylase.
Figure 7B:
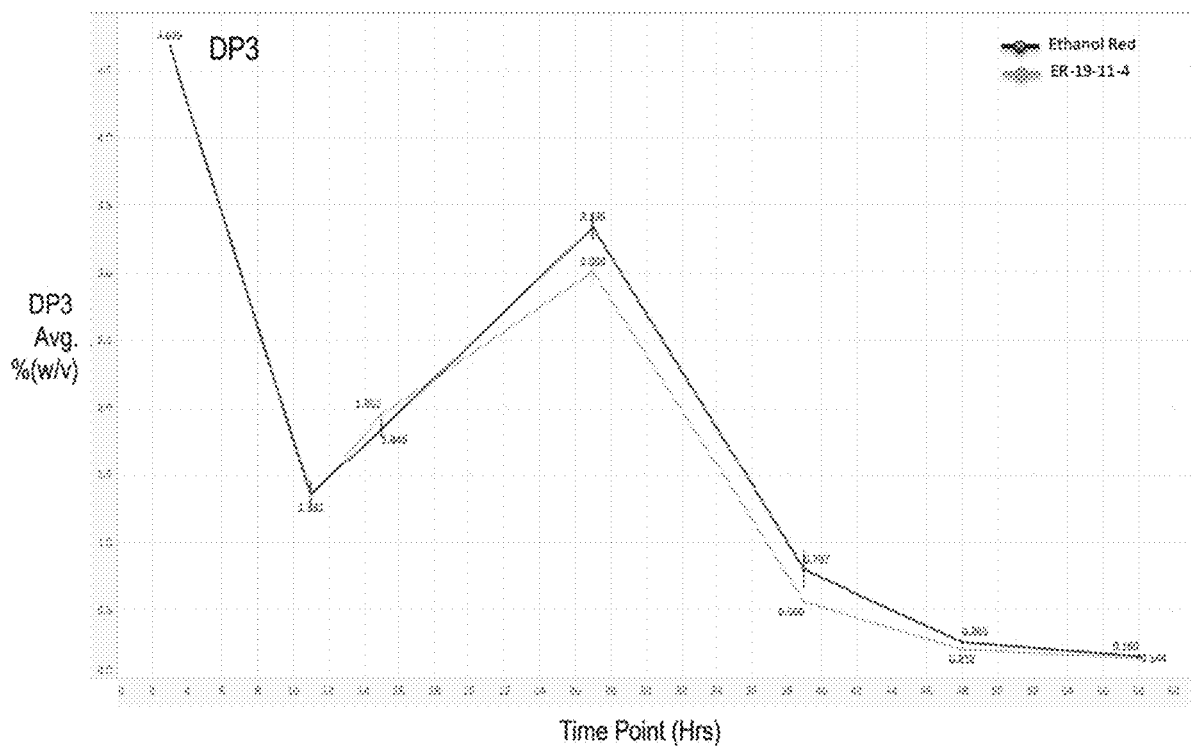
FIG. 7B. A graph illustrating the changes in DP3 levels from wild type and the maltophilic strain under conditions of maltose and glucose co-fermentation when corn mash is treated with Spirizyme Achieve Glucoamylase.
Figure 7C:
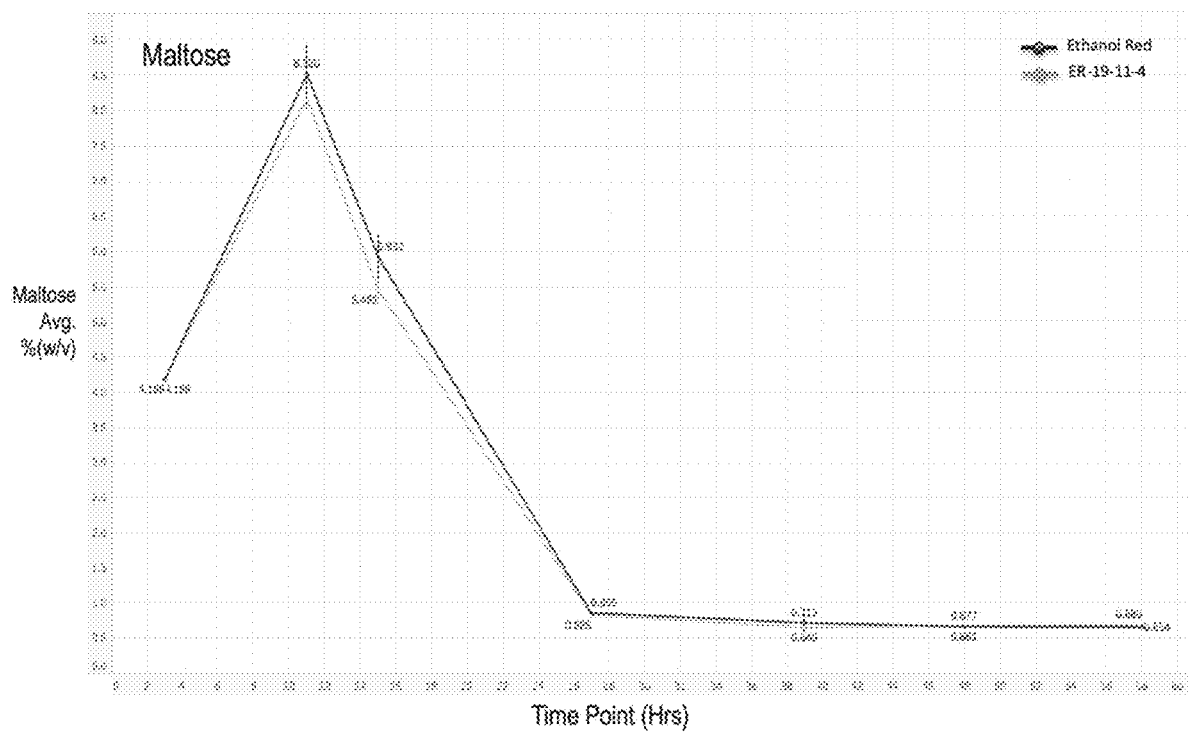
FIG. 7C. A graph illustrating the changes in maltose levels from wild type and the maltophilic strain under conditions of maltose and glucose co-fermentation when corn mash is treated with Spirizyme Achieve Glucoamylase.
Figure 7D:
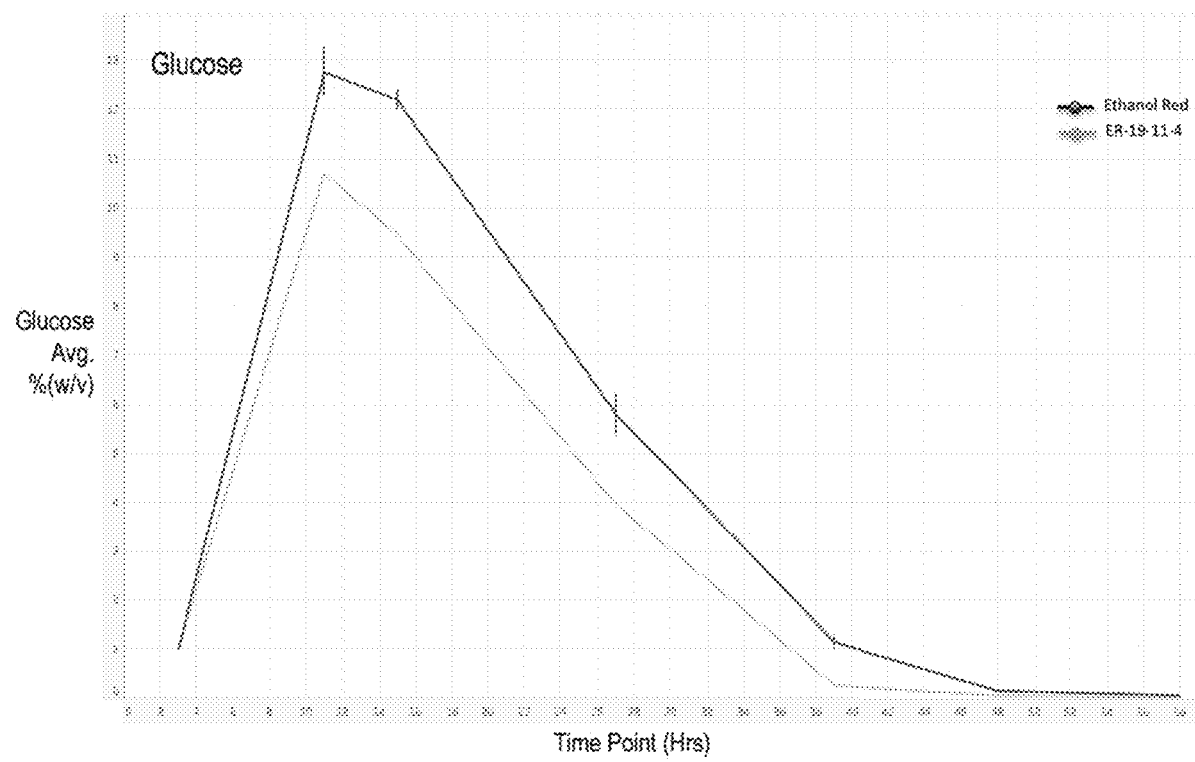
FIG. 7D. A graph illustrating the changes in glucose levels from wild type and the maltophilic strain under conditions of maltose and glucose co-fermentation when corn mash is treated with Spirizyme Achieve Glucoamylase.
Figure 7E:
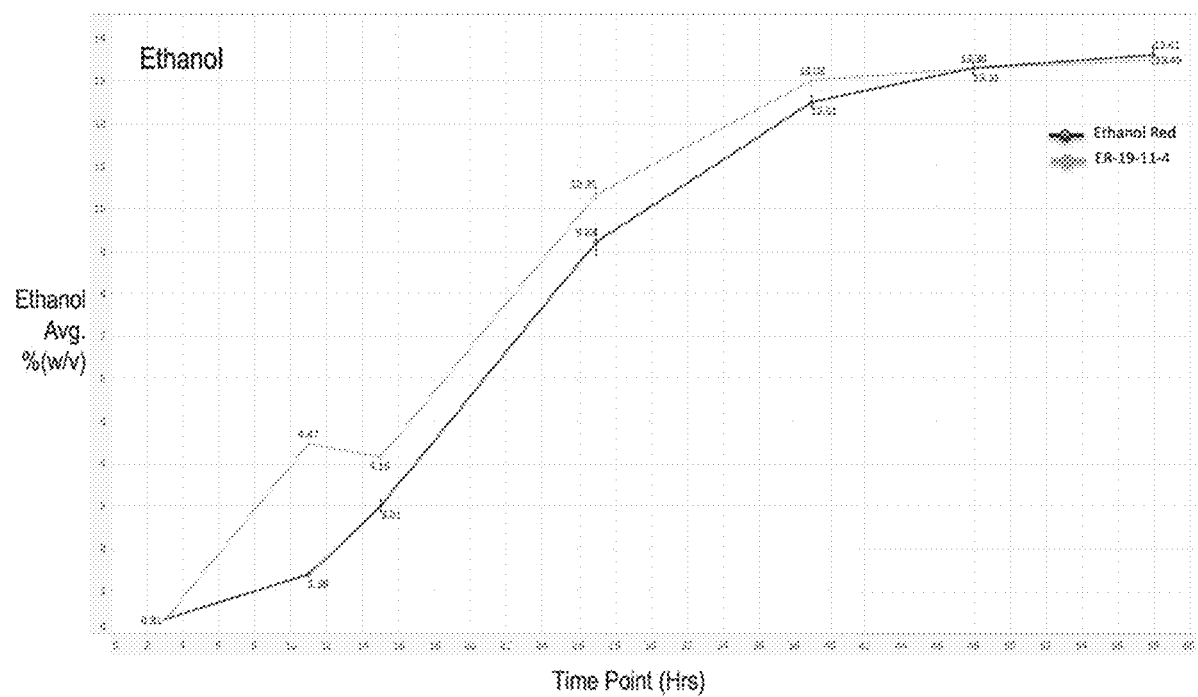
FIG. 7E. A graph illustrating the changes in ethanol levels from wild type and the maltophilic strain under conditions of maltose and glucose co-fermentation when corn mash is treated with Spirizyme Achieve Glucoamylase.

As a third test, corn mash with 32.6% solids was treated with (0.07% w/w) of Spirizyme Achieve Glucoamylase (Novozymes). This higher glucoamylase enzyme treatment resulted in even higher glucose levels along with higher final ethanol levels (FIGS. 7C-E). Under these conditions, maltophilic yeast ER-19-11-4 consumed maltose slightly faster and again produced more ethanol than an isogenic wild type strain (FIG. 7E). ER-19-11-4 also showed significant improvement in the rate of glucose consumption (FIG. 7F).

Figure 8A:
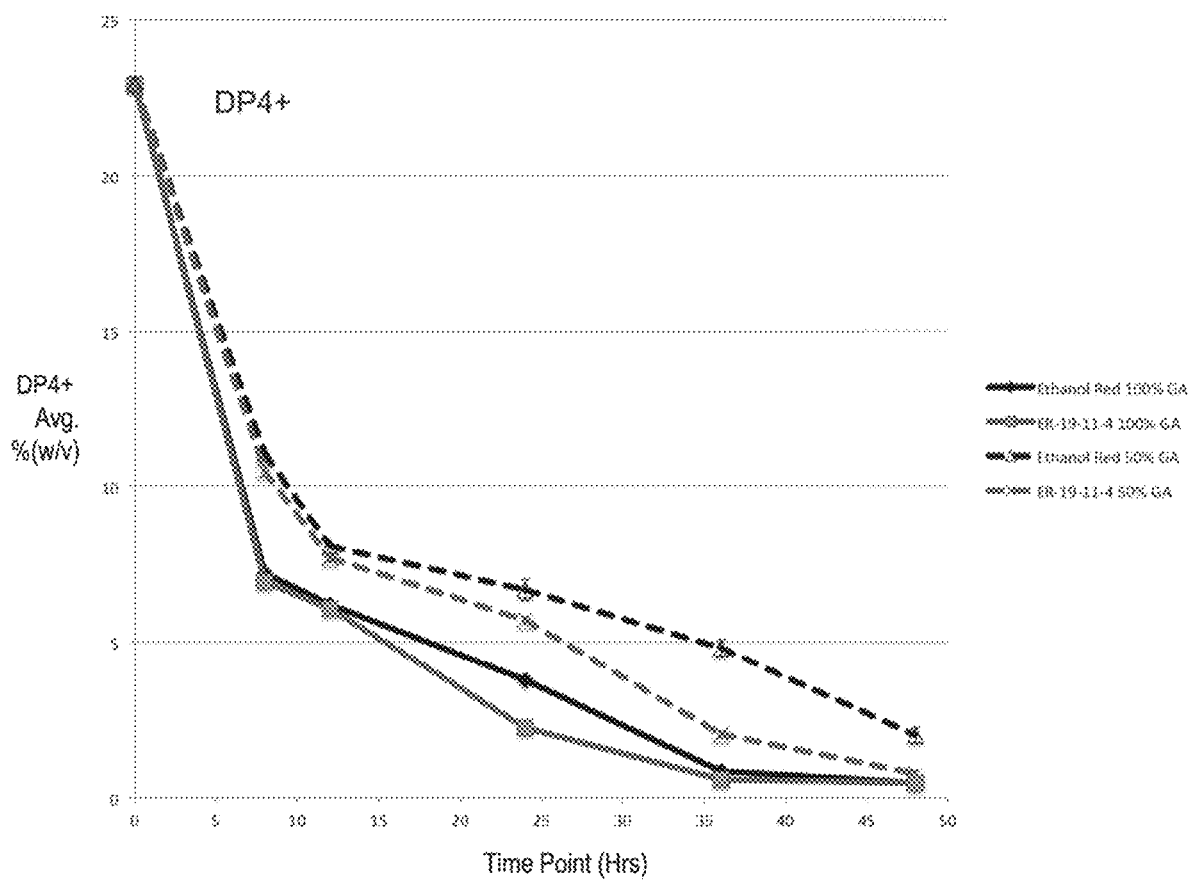
FIG. 8A. A graph illustrating the changes in DP4+ levels from wild type and the maltophilic strain under conditions of maltose and glucose co-fermentation when corn mash is treated with Spirizyme Achieve Glucoamylase at either 0.06% or 0.03% (w/w).
Figure 8B:
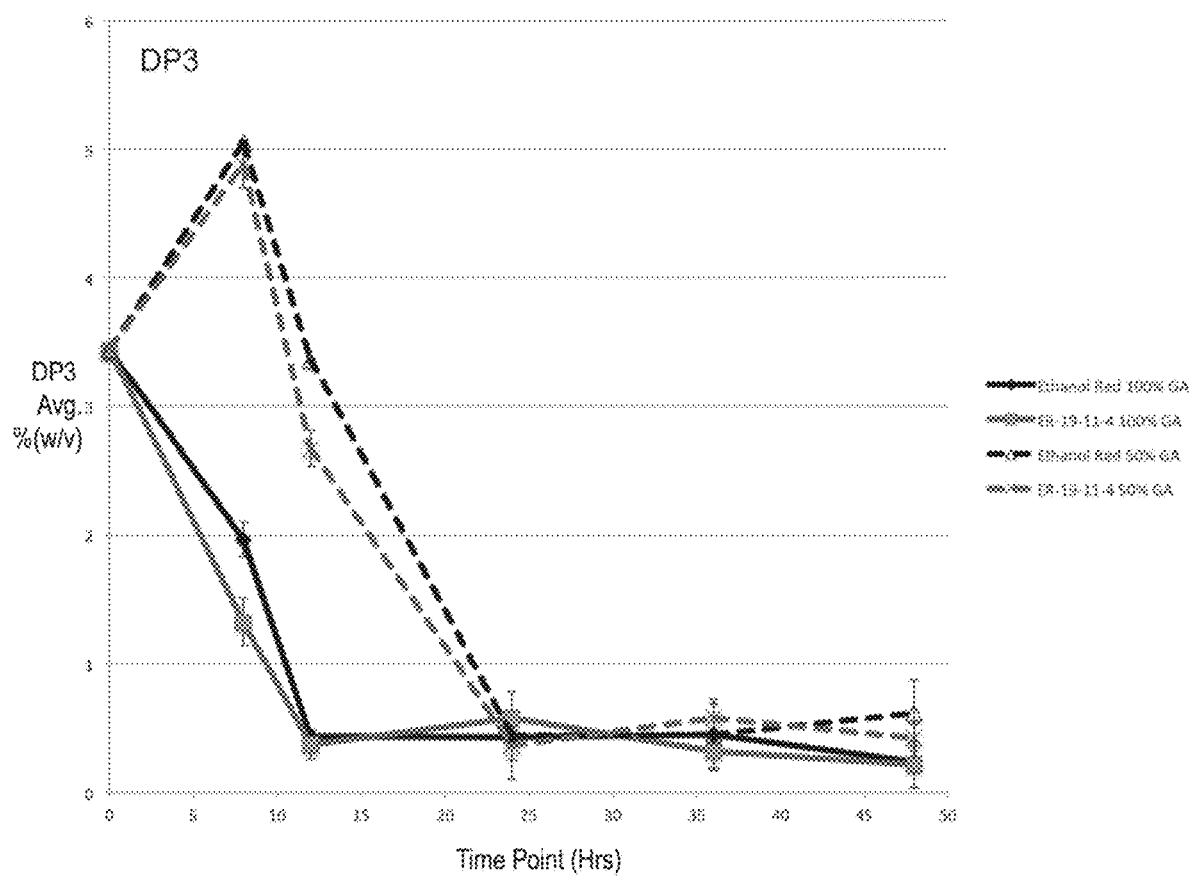
FIG. 8B. A graph illustrating the changes in DP3 levels from wild type and the maltophilic strain under conditions of maltose and glucose co-fermentation when corn mash is treated with Spirizyme Achieve Glucoamylase at either 0.06% or 0.03% (w/w).
Figure 8C:
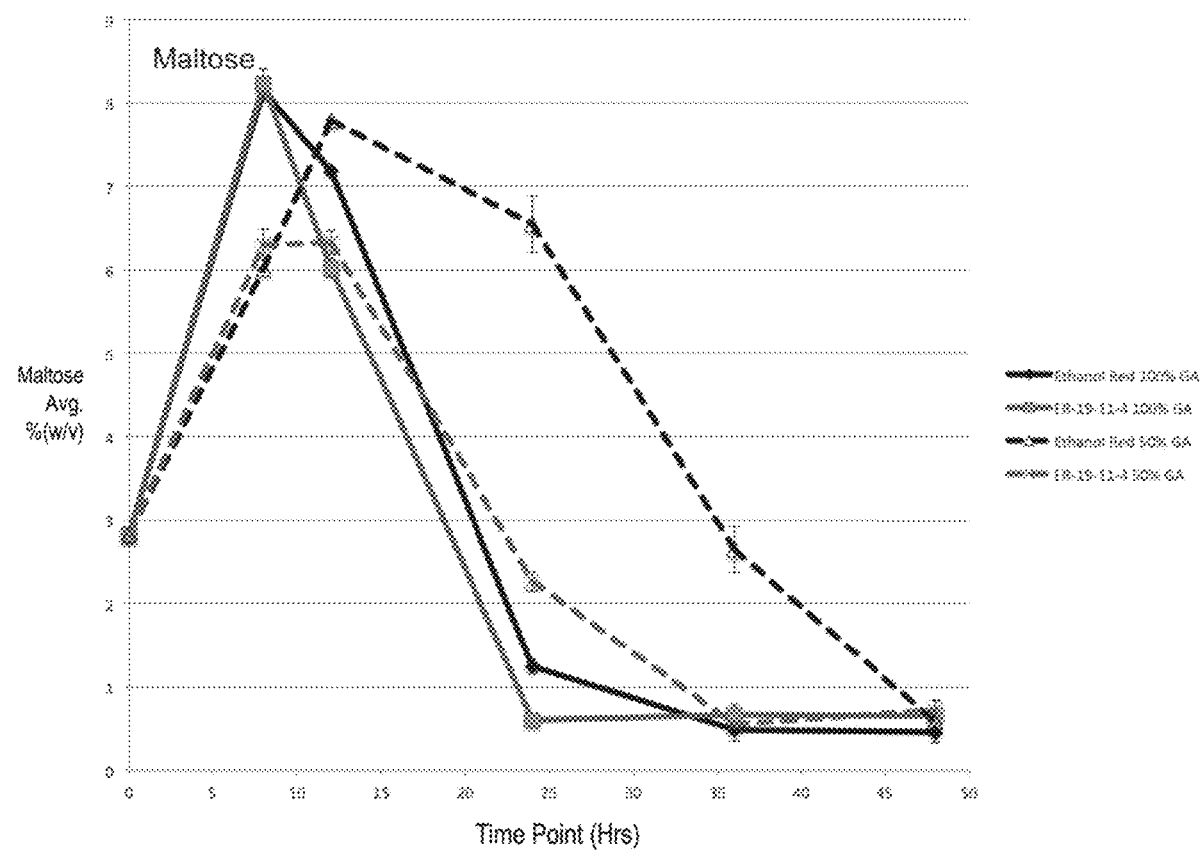
FIG. 8C. A graph illustrating the changes in maltose levels from wild type and the maltophilic strain under conditions of maltose and glucose co-fermentation when corn mash is treated with Spirizyme Achieve Glucoamylase at either 0.06% or 0.03% (w/w).
Figure 8D:
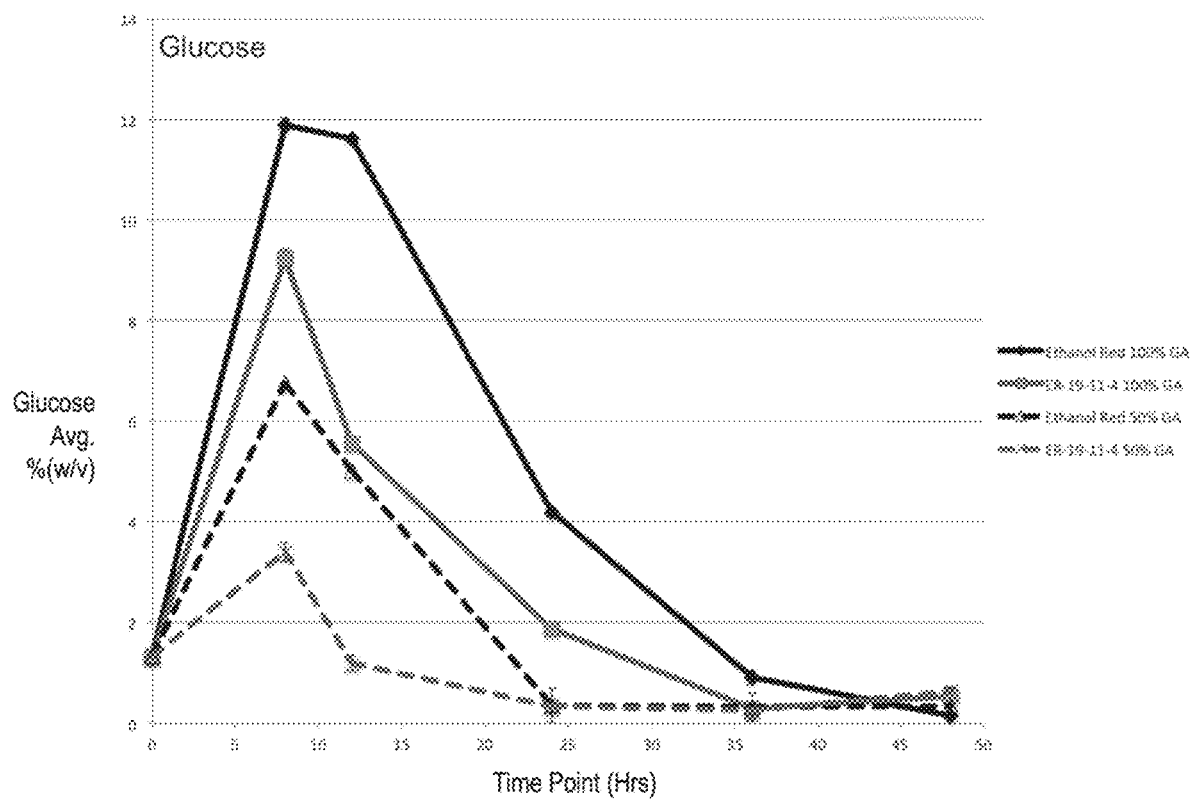
FIG. 8D. A graph illustrating the changes in glucose levels from wild type and the maltophilic strain under conditions of maltose and glucose co-fermentation when corn mash is treated with Spirizyme Achieve Glucoamylase at either 0.06% or 0.03% (w/w).
Figure 8E:
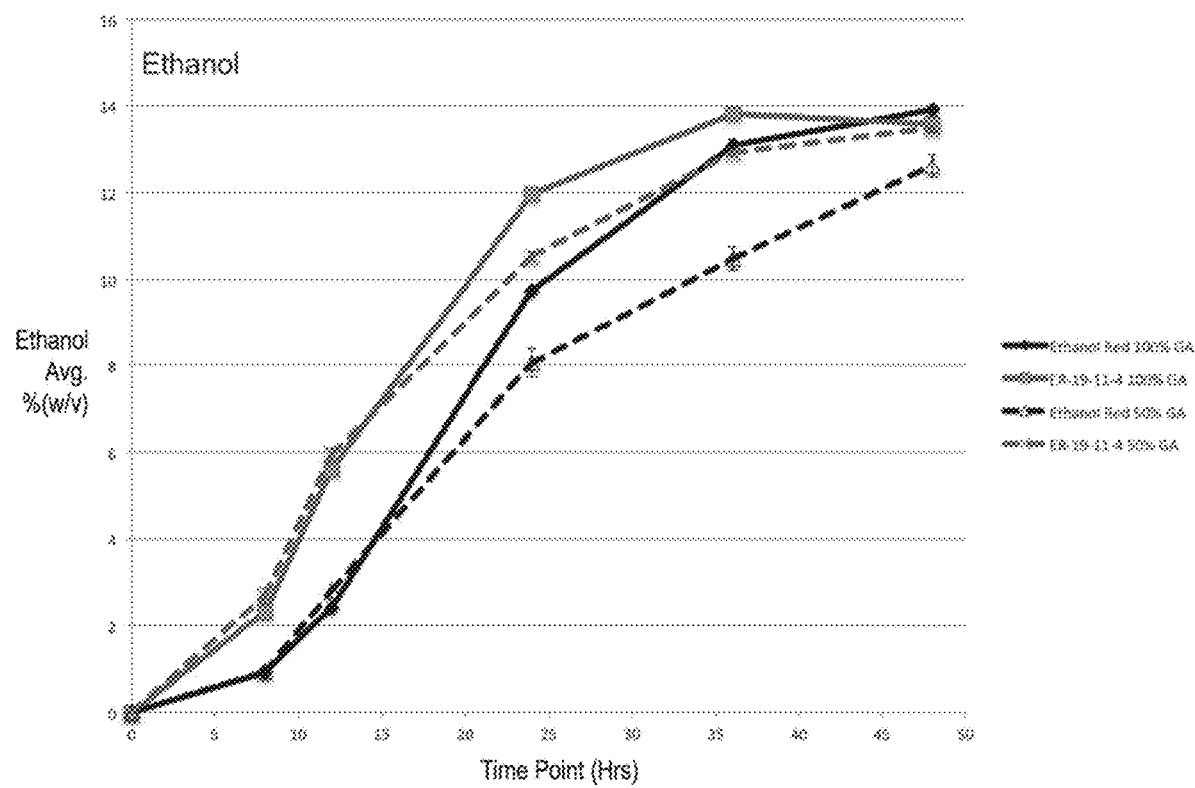
FIG. 8E. A graph illustrating the changes in ethanol levels from wild type and the maltophilic strain under conditions of maltose and glucose co-fermentation when corn mash is treated with Spirizyme Achieve Glucoamylase at either 0.06% or 0.03% (w/w).

As a final test, corn mash with 32% solids was treated with either a full dose (0.06% w/w) of Spirizyme Achieve Glucoamylase (Novozymes) or a half dose (0.03% w/w). Again, at the GA dose, ER-19-11-4 consumed DP4+, DP3, maltose and glucose faster and reached maximal ethanol levels at least 10 hours earlier than wild type at an increased rate (FIG. 8A-E). Reducing the amount of glucoamylase represents a chance for significant cost savings for fuel ethanol plants. In fermentations with a half dose of GA, excess DP4+ sugars remained at fermentation finish for the wild type strain, resulting in lower final ethanol concentration. Importantly, at 50% GA, the ER-19-11-4 strain allows for full DP4+ consumption and produces final ethanol concentrations equivalent to the wild type strain at 100% GA (FIG. 8A, E). The rate of ethanol production is also quicker for the ER-19-11-4 at 50%. This opportunity for enzyme cost savings was unexpected prior to experimentation and we suspect that increased rate of glucose and maltose consumption by the maltogenic strain allows the glucoamylase to work more efficiently. Overall, ER-19-11-4 shows improved maltose and glucose consumption and in turn increased ethanol yields over a wide range of fermentation conditions. Furthermore, this strain requires significantly less glucoamylase than the amount used with other leading industrial strains.

SEQUENCE LISTING

SEQ ID NO: 1. A Typical MAL1 Gene Cluster in the *S. cerevisiae* Strain Fermentis Ethanol Red®

```
FEATURES         Location/Annotation
gene             1414...2820/"MAL13"
gene             complement(3529...5373)/"MAL31"
gene             6218...7972/"MAL12"
     1   cacccagcc atcgtcatta gagtctttga aacttgctgg gtaaatttga tagaacgtgg 61   cctctttcca ccactttggt tctgtctctg gatgtgcaga agaaatagtc atcgatagta 121   aatattacgt tgaaaagctt tgtttgtatc ttgtttgatc tgtgcttgct cgattaattt 181   gagacagctt ttttatttca aaacaggcgt ctaaccaaac gtctagcaac tcaatatcat 241   tgcccttaag tacttttat ttcaaaagga gatcctttct cattctgggg taaactatgg
```

-continued

```
 301  tatgacgaaa accatgaaaa ataaggaaca taatttatcc gagtatttca acgatcccaa
 361  gtactgacat aaactttagt agccaattta tagcgtgggg tgcctacttc gtcacatttg
 421  atatcgtaca gcgaaaaaac attagtaact ttatttcctt atttcagggc acttttctc
 481  gagaataacg ctgcgtgctg agcggttgtt cacaccgcgg agttggaaac tttattctcc
 541  gaaatattct ccccactaaa atatccttac gtattgtgaa acttagtttt ctttttgtat
 601  tagggtgtaa tttcttattt tccctgtatt tcaccgcatg caaattctta cgatatttac
 661  tccggtaaac gcagttaaga gctattgtcc ggtccgactg aatgaatatt cggttagaaa
 721  cgcatatttg tggggaaata acaacctcaa agatatagac ggagcagtac cgtaaggttt
 781  acagaatggc atgaccaccc acaataaagc aaggacctcg agacacatgc ctttcaaaat
 841  agaaataaag gttttcgaac atcattttc gcttgttgta tagtagtctt tacagtaaca
 901  gtgcatctga gtacaggaac gattgtcttg ataatatgtg aaaagtgcac acaaaattag
 961  agggtgtcct ttacaagtat tcttagaaac acattcaaga gcacaaaagt cgatgcttta
1021  agggtcaagg tggtggaaaa cttgactgga attcttgacg aaaaaacaag aaaaacgtga
1081  ttcgagcaat cataaacata cagccccgtt ccaaccggat cttgaggttt cccatttag
1141  atggaaataa gcagagcaaa ataaaaatct tgaacaagta atagtggtga ctgcaggtta
1201  cgttggcata taaagtccgg gtgacctggg tttcctgcac caccagcccc catatgctag
1261  cacaatgggt tttctttatc cccggtcata attactcatt tgctatatt cttcataact
1321  taagtacgca gatagagaaa attaataatc tcgatatata ttaaagtaaa tgaaaagtag
1381  aaaatttagc cagaactctt ttttgcttcg agtatgactt taactaagca aacatgcgcc
1441  aagcaggcat gcgactgctg tcgtattcgt cgagtgaaat gcgatggtaa aaggccgtgt
1501  agcagttgcc tacagaatag tttggattgc acttatctgc aaccgtcgag aaaaagaggt
1561  ccgaagtcca ttaggttgag gagcttgaaa agaatagcag aagtgcagag ggaaagcggt
1621  cctaacacca ttgcaactgc tcctgtaata tataagaggg ttcccaaaaa gctaatcgat
1681  cagtgcttgc ggctctatca cgataattta tacgtaatct ggcccctct ttcgtacgat
1741  gaccttcaca aacttctgga ggaaaaatac aatgacaatt acgtatattg gtttctgacc
1801  gctttatcag cggccaccct cagtgattta caaactgaaa taaaatctga agaggaagtc
1861  acttcacgg gaaaacggtt atctaatctt tgcatctcat cgtgtcagca attcgacgat
1921  ttggataaca gcaatatatt caatattatg acgtactact gtttgcatcg tagctttgca
1981  caaatatcga acgcaagaac ttcttacaga ctctgttgtg aagcggtcgg tctgattacg
2041  gtagcagggt tacatcggga agaaacttac ggatccctta catttgaaga acagcaactt
2101  agacggaaac tttattactt gcttctcatg acgagagat actatgccat atatcttcat
2161  tgtgcgacga gcctggatgc cacaatagca ccaccgcaac ttgaacttgt aactgatcct
2221  cagctttcta tggacagttt ccttgaaatg attagggtat ttactgtacc aggaaaatgt
2281  ttcttcgatg ctttagccgc tgactctaca gatgcttctt gcactgaaga gtcattgaaa
2341  aagatatgga aagagctcca tacagcatca ttagaaatag agccgtggtc ttacggttac
2401  gttgacattg cattttccag gcactggatt agagtcctcg cttggaagct agtcttgcgg
2461  acaggaaata tcaacttcct atccgcctct aacagtgcac atgtaccact tgaaattgca
2521  agggatatgc ttgacgacgt gtttctaaca ccaaataatc tttatggagt tcatggccct
2581  gggataccaa caaaggcaat agaagtagcc aatgcactag tggatgtcat gaatcagtat
```

-continued

```
2641   gatcaagata ctgaatcaga ggcttggaaa gttttgtgcg aaatttccaa atttgtcttc
2701   tctttaaaac aatacgatgg aaaactggtt gaaaattttg tgactaaatg tcagagcgct
2761   cttattactc ttccaatctc taaacctttg aaaaaaaatg aagatttgca taaaatatga
2821   ctcactttaa tttcttgagt gaacattttt catccatttc ttcatgtaaa ctccaaaaaa
2881   gaaagcttct gtcggtttta agataaaagt actcctcgtg tataggaata tttttatctt
2941   tgttagctct gtagaaaaag atacagataa agctcctgta atatttgttg cagattttttg
3001   gtccatgaat tatttttatca cgatcgaaaa gaagttatgt tcgttatatc cagtggaaaa
3061   agcattgtta tatgatggag tccggtgcct gtctctgcat aaaaaaataa catttttaata
3121   catgggaggt gttatattgt acagagagga gacaatgata tggctttgtt ggtgttgtat
3181   gactaacata gggcgttttt atgattcatg aaatttattt aatacatgtt tacgattttta
3241   actattgtga atacattgct attgtatata tgtaatcata tcagcaattc tagcatttta
3301   acatgtgact tgagctggat gattaaaata tgttaatttt tttagaatta ttatctagta
3361   caacaactac cagaatagtt gaactgaata atatcaaatg aaaaggactc ctctagctga
3421   attttggaat gtttgccaaa taaaaaaaag actttataac aaaaggttaa ttaaatgtat
3481   ttagtaaaaa aaaaaaagtt tgtcatattt atctattgaa atgaagtatc atttgttcac
3541   aacagatgag gtgcttcgcc cttcatctac cacagaagtt tccaaatctt ccttcggatc
3601   tttaacatta atttctgcag ctgctgcttt ggcagctgca aaagggtcga ctttagtcga
3661   cttgaacttt cttgctggaa caccaagtct aaacaattca tttatctcaa taaaagtcct
3721   gccagcggtt tctggtaaat cgacaacagc ccaagctaaa gtggccagac aaaatcctcc
3781   ccagaaaaag cctgatttag cacccccaatt ccatttctct gagttcaatt ggtacatgat
3841   caaaactgta actacaactt ggatcacatt gtaagcatta cgagccaaaa taattgtttt
3901   ggttcttagc cttgaagacg gtatttcaga cactaagcaa aaaacaacag gtgcaatacc
3961   gaggttgtaa agaacgcga caaccattag aagagcacca ctacccattt tagcgccatg
4021   agtgtctgaa catcctaaac caccgataat gaagaacata atagcctgaa aagccagccc
4081   aaaagcataa aggtcaaatc tgccacaata ttttgaagcc caccaggata taaacgttgc
4141   agcaatacca agacaatatt ggataatact gaaagtaaaa gccgtatcag tgctaacacc
4201   agcttttttca taaaagtaag ttgaataacc aattaatgat gcaccacagg agcattgacc
4261   gatccaacat aaacaagcta ttctcgttct tctcctgtta ataccatctt tcacacaatc
4321   ccagtaagtt ccttcatcag acatttctg ctccttttct atagtagttt tgattttatc
4381   gagttccata ctcactagta attctttctc gggtccttta ccacttaatg ttctttcaag
4441   tgatctcctc gcttgatcaa tccttccttt tttaaccagc caccatggag actctggtgc
4501   aaaaaaaata cctaccgcca aaggaagggg ccagatccac tgcaaagcaa aaggtagctt
4561   atatcctagt tctgagttgg catatttgtt ctgggaattt ttcataatac cagcagcgaa
4621   aagttgaccg aacgcccaac ataaattaga ataagtcgtc aaatagtatc ttagggccaa
4681   aggacaaatt tcagaagcat aagaaacggt caaacattgg aaacaacccc atggcatacc
4741   acacaatgcc tgtcccacgg caatcatacc caaactcttg caaaaataca gaatgaaaat
4801   gaaagccgct aaaaagaaca acgccatgat cagagtgtaa cggttgccca tgtaatctac
4861   agaaggccca gtcatttgca aaccgacaat ctcacctgcc atgtagcata gacatagacc
4921   gatttgccag gaaactgaaa tttcataatc tcctgtattg ctattcaaag aaccatattt
4981   ttttttgaaaa acaggcaggg catagaaagc tcctagaatg gctgtgtcat aaccctcttg
```

```
5041  aatcaatgtt gtggaaacta atagtgacca agcagcagct tttggatatg tcttcaaagc
5101  tgtcatgagt ggcattcccc tctcactttc atctgcctct ttggcgtcct gcatagcttc
5161  atcgagaagg tcggggactt cttcattatt atcgtttggt attagtgaac ctggaccgta
5221  ctcaagatgg gaaagatcaa atcactttt cttaccttgc tcctccatct ctatcgagtt
5281  gaattcggta gcgttcacgc cattctcgat ctcatctaag tgtgagtcgt tcctgtcttt
5341  ttttctgttt attaatgagg ataatcccct catagttaat taatagtctt ggatgtaatt
5401  cttattgtta tactgaatat gctaaaacca ctcacaacaa gtatggagta tattgtgcct
5461  ctttatatcc tgagtactta tgcaatatgc gctcactcag gatgaaatgt acacagccga
5521  aagtatattg aaagctgcct ctgcggaaac ttctatctaa tgttgtctcc agatgtagac
5581  tatgaggcct gaagaagtct ttaagcaccct gttggagagt ataaggagac tgctacaaca
5641  acgtcttccc cacaaaaaat tatgtggagg ccgctatgat acctgcacaa acgttaagtt
5701  acacatgaaa aagagactga cataactttg atctctgaaa atatgttttc cccgagtagc
5761  ttcactgctt ggataccaat acgaatagac cttggctata gtaagttgcc tctgtaccgt
5821  agagattctt gcaacctcgc ttaaactctc gctttatca aatttcgcta aacacggggt
5881  ttaagttaaa gtttacagga tttatccgga aattttcgcg acccccacac aattaagaat
5941  tggctcgaag agtgataacg catacttttc ttttcttttt ttagttccta gcgtacctaa
6001  cgtaggtaac atgatttgga tcgtgggatg atacaaacaa cgtaagatga atagttcctt
6061  cctcaattct tcttgcagca tcatttctt gaggcgctct gggcaaggta taaaaagttc
6121  cattaatacg tctctaaaaa attaaatcat ccatctctta agcagttttt ttgataatct
6181  caaatgtaca tcagtcaagc gtaactaaat tacataaatg actatttctg atcatccaga
6241  aacagaacca aagtggtgga aagaggccac aatctatcaa atttacccag caagttttaa
6301  agactccaat aacgatggct ggggtgattt aaaaggtatc acttccaagt tgcagtatat
6361  taaagatctt ggcgttgatg ctatttgggt ttgtccgttt tatgactctc ctcaacaaga
6421  tatggggtat gatatatcca actacgaaaa ggtctggccc acatacggta ccaatgagga
6481  ctgttttgag ctaattgaca agactcataa gctgggtatg aaattcatca ccgatttggt
6541  tatcaaccac tgttctacag aacacgaatg gttcaaagag agcagatcct cgaagaccaa
6601  tccgaagcgt gactggttct tctggagacc tcctaagggt tatgacgccg aaggcaagcc
6661  aattcctcca aacaattgga aatctttctt tggtggttca gcttggactt ttgatgaaac
6721  tacaaatgaa ttttacctcc gtttgtttgc gagtcgtcaa gttgacttga attgggagaa
6781  tgaagactgc agaagggcaa tctttgaaag tgctgttgga ttttggctgg accatggtgt
6841  agatggtttt agaatcgata ccgctggttt gtattcgaaa cgtcctggtt taccagattc
6901  cccaattttt gacaaaacct cgaaattaca acatccaaat tgggggtctc acaatggtcc
6961  taggattcat gaatatcatc aagaactaca cagatttatg aaaaacaggg tgaaagatgg
7021  tagagaaata atgacagtcg gtgaagttgc ccatggaagt gataatgctt tatacaccag
7081  tgcagctaga tacgaagtca gcgaagtttt ctccttcacg cacgttgaag ttggtacctc
7141  gccattttc cgttataaca tagtgcccct caccttgaaa caatggaaag aagccattgc
7201  atcgaacttt tgttcatta acggtactga tagttgggct accacctaca tcgagaatca
7261  cgatcaagcc cggtcaatta cgagatttgc tgacgattcg ccaaagtacc gtaaaatatc
7321  tggtaagctg ttaacattgc tagaatgttc attgacaggt acgttgtatg tctatcaagg
```

-continued

```
7381  tcaggagata ggccagatca atttcaagga atggcctatt gaaaagtatg aggacgttga
7441  tgtgaaaaac aactacgaga ttatcaaaaa aagttttggt aaaaactcga aggaaatgaa
7501  ggatttttt aaaggaatcg ccctactttc tagagatcat tcgagaactc ccatgccatg
7561  gacgaaagat aagcccaatg ctggatttac tggcccagat gttaaacctt ggttttctt
7621  gaatgaatct ttcgagcaag gaatcaatgt tgagcaggaa tccagagatg atgactcagt
7681  tctcaatttt tggaaaaggg ccttgcaagc cagaaagaaa tataaggaac ttatgattta
7741  tggttacgat ttccaattca ttgatttaga cagtgaccag atctttagct tcactaaaga
7801  gtacgaagac aagacgctgt ttgctgcttt aaatttcagt ggcgaagaaa ttgaattcag
7861  cctcccaaga gaaggtgctt ctttatcttt tattcttgga aattatgatg atactgacgt
7921  ttcctccaga gttttgaaac catgggaagg tagaatctac ctcgtcaaat aaaattagtg
7981  ccggcttttt tttagcgcgt actttaacga aataacacat gattttcac atgattttg
8041  ttagataaat tttttatatg taaatgatga tagcgtaaaa gcactgttga taattttgttt
8101  caccattatg ggtaaatgtg tttttctaca tgaccctcgt tcattatgat atttagcgtg
8161  tatataaatg tgaattccaa attattaatg aggcataaga agcactatcc tttctcttcg
8221  gatgaaaaca agggagaaga aacctgtgct ggtattaatg ctgaaatgtc ttgctaagaa
8281  tcatacaagg tggtagtttt atttaataaa gaaaagaaaa ggactagata taaaagtga
8341  aatgaatata agatagcgtt aagagatgtc cgcagtactt gacacataat ttagcgtttt
8401  ctcgggaagc tctgtgattt tatgattcaa taacacagcg taattgattt cgtgatagtt
8461  cgatcctata tgtaatctca cgtaacactc aggcgagtta caaaatcgat tcaacattgc
8521  cggcttatgc gtttacgtca agtctgagca tgcctacccc cttccgaacc cgccttttat
8581  tgtctagcct tcagatgaac taaaccaatc atctgtccat aattcctctg ctttagacag
8641  tgttattaag caaagaaaa taagcgcata agattcttgc tacttcagta actccacaac
8701  attaacaccc cacaatcaat atctaaaagc caatgaag
```

40

SEQ ID NO: 2. Engineered Vector Sequence with Typical MAL1 Gene Cluster From Cen.PK Strain 113-7D

```
FEATURES           Location/Annotation
misc_feature       1...500/"500 bp 5' MAL13"
CDS                502...1923/"mal13"
misc_feature       1924...2261/"300 bp 3' MAL13"
misc_recomb        complement(2292...2325)/"LoxP"
misc_feature       2326...2706/"TEF promoter"
misc_feature       2707...3735/"Hygromycin B_Resistance"
misc_feature       3736...3968/"TEF terminator"
misc_recomb        complement(3969...4002)/"LoxP"
misc_feature       4024...4325/"300 bp 3' MAL11"
CDS                complement(4326...6176)/"MAL11"
CDS                6962...8716/"MAL12"
misc_feature       8717...9216/"500 bp 3' mal12"
    1  acaggaacga ttgtcttgat aatatgtgaa aagtgcacac gaaattagag ggtgtccttt
   61  acaagtattc ttagaaacac attcaagagc acaaaagtcg atgctttaag ggtcaaggtg
  121  gtggaaaact tgactggaat tcttgacgaa aaacaagaa aaacgtgatt cgagcaatca
  181  taaacataca gccccgttcc aaccggatct tgaggtttcc catttttagat ggaaataagc
  241  agagcaaaat aaaaatcttg aacaagtaat agtggtgact gcaggttacg ttggcatata
  301  aagtccgggt gacctgggtt tcctgcacca ccagccccca tatgctagca caatgggttt
  361  tctttatccc cggtcataat tactcatttt gctatattct tcataactta agtacgcaga
```

```
 421  tagagaaaat taataatctc gatatatatt aaagtaaatg aaaagtagaa aatttagcca
 481  gaactctttt ttgcttcgag tatgacttta actaagcaaa catgcgccaa gcaggcatgc
 541  gactgctgtc gtattcgtcg agtgaaatgc gatggtaaaa ggccgtgtag cagttgccta
 601  cagaatagtt tggattgcac ttatctgcaa ccgtcgagaa aaagaggtcc gaagtccatt
 661  aggttgagga gcttgaaaag aatagcagaa gtgcagaggg aaagcggtcc taacaccatt
 721  gcaactgctc ctgtaatata aagagggtt cccaaaaagc taatcgatca gtgcttgcgg
 781  ctctatcacg ataatttata cgtaatctgg cccccttctttt cgtacgatga ccttcacaaa
 841  cttctggagg aaaaatacaa tgacaattac gtatattggt ttctgaccgc tttatcagcg
 901  gccaccctca gtgatttaca aactgaaata aaatctgaag aggaagtcac tttcacggga
 961  aaacagttat ctaatctttg catctcatcg tgtcagcaat ttgacgattt ggataacagc
1021  aatatattca atattatgac gtactactgt ttgcatcgta gctttgcaca aatatcgaac
1081  gcaagaactt cttacagact ctgttgtgaa gcggtcggtc tgattacggt agcagggtta
1141  catcgggaag aaacttacgg atcccttaca tttgaagaac agcaacttag acggaaactt
1201  tattacttgc ttctcatgac ggagagatac tatgccatat atcttcattg tgcgacgagc
1261  ctggatgcca caatagcacc accgcaactt gaacttgtaa ctgatcctca gctttctatg
1321  gacagtttcc ttgaaatgat tagggtattt actgtaccag gaaaatgttt cttcgatgct
1381  ttagccgctg actctacaga tgcttcttgc actgaagagt cattgaaaaa gatatggaac
1441  gaactccaca caacttcctc ggaaatagag ccatggtcta acggttacat agacatctca
1501  ttttcccggc attggattag gatactagca tggaagctag cttatcaaat gaggggtagc
1561  aacttttcat tgaacgctaa caatgggcaa ataccaatag aaattgcgag agatatgtta
1621  atagacactt acttaacccc agagaatctt tacgatgtcc atggtcccgg ggtaccagtg
1681  aaaacattag aaatagctac tgctttggtg gacattgtag gccagtatga tcataacatg
1741  aaattagaag catggaatgt tttgcatgat gtatgcaaat ttgctttttc tttaaaccac
1801  tataacaatg atatgctgaa gagattttcc accaaatgcc agaatgccct aattactctg
1861  cccatttcta aacctttaca attggatggt tatcccaagg ataatgaaga catagaccct
1921  tgattaattt tcattttgt gcatctcaac ttcctggtaa gtgatagctt tccattgtag
1981  aaactgtgtt tccgcaacac aagggtaaaa ttcactgcta attgcgaccc attttcatga
2041  acagagtaat taattttcta tttggaggtc tacttttaca agtataagac tgcttcttac
2101  catgatgtct ccctattgaa aattatattt aataaaatac ttttaggcac gctaacgtta
2161  gcattcttcc cagaattcct atactaacag ttttcagtat atatacactt ttttactgag
2221  tgctaagagc cagattggat gagatgattg tgtactgatg gagaattaac ggttggagag
2281  ctattactca cataacttcg tataatgtat gctatacgaa gttatttagc ttgcctcgtc
2341  cccgccgggt cacccggcca gcgacatgga ggcccagaat accctccttg acagtcttga
2401  cgtgcgcagc tcaggggcat gatgtgactg tcgcccgtac atttagccca tacatcccca
2461  tgtataatca tttgcatcca tacattttga tggccgcacg gcgcgaagca aaaattacgg
2521  ctcctcgctg cagacctgcg agcaggaaa cgctcccctc acagacgcgt tgaattgtcc
2581  ccacgccgcg cccctgtaga gaaatataaa aggttaggat tgccactga ggttcttctt
2641  tcatatactt cctttttaaaa tcttgctagg atacagttct cacatcacat ccgaacataa
2701  acaaccatgg gtaaaaagcc tgaactcacc gcgacgtctg tcgagaagtt tctgatcgaa
2761  aagttcgaca gcgtctccga cctgatgcag ctctcggagg gcgaagaatc tcgtgctttc
```

-continued

```
2821  agcttcgatg taggagggcg tggatatgtc ctgcgggtaa atagctgcgc cgatggtttc
2881  tacaaagatc gttatgttta tcggcacttt gcatcggccg cgctcccgat tccggaagtg
2941  cttgacattg gggaattcag cgagagcctg acctattgca tctcccgccg tgcacagggt
3001  gtcacgttgc aagacctgcc tgaaaccgaa ctgcccgctg ttctgcagcc ggtcgcggag
3061  gccatggatg cgatcgctgc ggccgatctt agccagacga gcgggttcgg cccattcgga
3121  ccgcaaggaa tcggtcaata cactacatgg cgtgatttca tatgcgcgat tgctgatccc
3181  catgtgtatc actggcaaac tgtgatggac gacaccgtca gtgcgtccgt cgcgcaggct
3241  ctcgatgagc tgatgctttg gccgaggac tgccccgaag tccggcacct cgtgcacgcg
3301  gatttcggct ccaacaatgt cctgacggac aatggccgca taacagcggt cattgactgg
3361  agcgaggcga tgttcgggga ttcccaatac gaggtcgcca acatcttctt ctggaggccg
3421  tggttggctt gtatggagca gcagacgcgc tacttcgagc ggaggcatcc ggagcttgca
3481  ggatcgccgc ggctccgggc gtatatgctc cgcattggtc ttgaccaact ctatcagagc
3541  ttggttgacg gcaatttcga tgatgcagct tgggcgcagg gtcgatgcga cgcaatcgtc
3601  cgatccggag ccgggactgt cgggcgtaca caaatcgccc gcagaagcgc ggccgtctgg
3661  accgatggct gtgtagaagt actcgccgat agtggaaacc gacgcccag cactcgtccg
3721  agggcaaagg aataatcagt actgacaata aaaagattct tgttttcaag aacttgtcat
3781  ttgtatagtt tttttatatt gtagttgttc tattttaatc aaatgttagc gtgatttata
3841  ttttttttcg cctcgacatc atctgcccag atgcgaagtt aagtgcgcag aaagtaatat
3901  catgcgtcaa tcgtatgtga atgctggtcg ctatactgct gtcgattcga tactaacgcc
3961  gccatccaat aacttcgtat aatgtatgct atacgaagtt atgagtggta taacaagacc
4021  tgcaagtgta tggacattta aagtaacagt taattgagaa tacggttgac ctggcatgtt
4081  gttcgaatca atatccaggc acaagtacca ggtgctaaag aaaaagtact ctcatatttg
4141  cttgattgct gcttgggcta ttttaactaa ctactaacaa tattttgctt aaaaaatggt
4201  aaatatgaat gttttacaga aaaataaaaa atgtatatat ataaaatctc gagctagctg
4261  agggttttgg gagcagtcaa agggattcct tatttcttcc aaaaaaaaaa aaacaaccct
4321  tttacttaac atttatcagc tgcatttaat tctcgctgtt ttatgcttga ggactgactg
4381  atactctcat cagctagcga atcatgttga gttttttccct ttccgaatgg atcaaccaca
4441  gtagatgcaa attttctggc aggaacccct tggttgaaaa gttcattaat ttcactgaag
4501  gttctaccag ttgtctcagg cagatcgatg atgacccaag ctaaagtgac tgctgtgaaa
4561  ccaccccagt atagaccagt tttggcaccc cagttccaat cgctcacgtt tagcatatag
4621  ggcgttaata tagcgttaat aacggccatg agattgtagc aaatacgggc cagcactata
4681  gtcttagttc tcaactccgc tgatggaatt tcagcaacga tacagtaaac aactgcaccg
4741  ataccagcat tgtaaaagaa tgataaagcc agcaataaac caccggcacc attactagcg
4801  ctgcttccag aaccaaaacc cattccacca ataataaata agcagaccat ttgaaatgca
4861  agaccatagg tcagtattgt ccatctacca acacggccag atattaccca ggagcaaagt
4921  gtacccgcta acccaagaca gtactgaatt agagaaaaag taaacgcctt gtcggtggcc
4981  atacctgctc tttcaaaaaa atatgtcgag taaccaagta aaacggcacc gctactattt
5041  tgagctaccc aagttaaaca tgcaagtctc gttcttcttc cattaactcc cttgaaacaa
5101  ttaaagaatg atcctgattt agatgctaaa agtctttctt tttcaatagt caattcaatc
```

-continued

```
5161  tgctttaaag taagatcaac ttgaatgtcc ttctcggcgc ctttaccact caaaattctg
5221  cttaaagatt ttcttgcctc agcgaccta tcctttctca ccaaccacca gggcgactca
5281  ggagcgaaaa agataccgat cattaaagga gcaggccaaa tccattgtaa agcaaatggc
5341  aatttatagc ccaagtcgga gttccctaaa ttctcttgtg agtttttcat aataccagag
5401  gcgaagattt gaccaaataa ccaacaaatg ttggagtaac tggtcatgta atatcttaat
5461  gctaaaggc aaacttccga agcataagta acagccaaac tttggaaaca accccatggt
5521  atagctgaga gaatttgtcc cacagcaatc atagctaaac ttttacagta gtagaggata
5581  aagatataag cagttaacaa accaagtgct gtaatcatcg tataacgatt ccccataaat
5641  tcaaccatat aagtcgtgat ttgcaaacca atcatctcac cacaaaggac acacatgttt
5701  aaaccaatct gccattggga agtaatttcg taagaaccct ccccgttcaa agtaccgaat
5761  tttctctgaa aaactggcag ggcatacagt gcgctcagta gtgcggtatc ataaccttcc
5821  ataaccaggg tagtagacac taatatggac cacagggctg cttttggata ttttagcaac
5881  gcctgcttca aagtcatgct ttttcctcg ctgttagctt catttgcatc atcagtagcg
5941  ttcatctcat taatcacatt ctcgttatct tcgtcagaat ctcctaactg ggctgaattg
6001  gtggtgaact ctaagtggtc tagctcaaag gcactatcct ttttcccttc ttcaaaatct
6061  tcagtattga aaacctcctg ttggtttaca atatctcttg aagactcaga aatgttttta
6121  tcctcatttt ttgaggcagc cttcttcttg cttaccaatg aaatgatatt tttcatatta
6181  tactattttt ttagttgttt gatgttcttc tatgtagcat cagaaagaaa caccaacccg
6241  aaaattcttc aaacaatcaa taccaaaccg ctttatataa aaaattaaga tgtcgacatt
6301  ccttattttt tactgagttc gttaaagttg ggtacactct tgattactgt aattgtctct
6361  gtatgtccct caagcccggt acgttgtcat tttctagtac gcatcaacgg agtgttacat
6421  gatagataga ccgagtagaa tctatggcta tggggtaatt aaaaccttaa agctcctttc
6481  gctgccatag taatacgaat agaccttggc tatagtaagt tgcatctgta ccgtagagat
6541  tcttgcaact cgcttaaact ctcgctttta gataatattt ctccttattg cgcgcttcgt
6601  tgaaaatttc gctaaacacg gggtttaagt taaagtttac aggatttatc cggaaatttt
6661  cgcggacccc acacaattaa gaattggctc gaagagtgat aacgcatact tttcttttct
6721  ttttttagtt cctagcgtac ctaacgtagg taacatgatt tggatcgtgg gatgatacaa
6781  acaacgtaag atgaatagtt ccttcctcaa ttcttcttgc agcatcattt tcttgaggcg
6841  ctctgggcaa ggtataaaaa gttccattaa tacgtctcta aaaaattaaa tcatccatct
6901  cttaagcagt ttttttgata atctcaaatg tacatcagtc aagcgtaact aaattacata
6961  aatgactatt tctgatcatc cagaaacaga accaaagtgg tggaaagagg ccacaatcta
7021  tcaaatttac ccagcaagtt ttaaagactc caataacgat ggctggggtg atttaaaagg
7081  tatcacttcc aagttgcagt atattaaaga tcttggcgtt gatgctattt gggtttgtcc
7141  gttttatgac tctcctcaac aagatatggg gtatgatata tccaactacg aaaaggtctg
7201  gcccacatat ggtaccaatg aggactgttt tgagctaatt gacaagactc ataagctggg
7261  tatgaaattc atcaccgatt tggttatcaa ccactgttct acagaacacg aatggttcaa
7321  agagagcaga tcctcgaaga ccaatccgaa gcgtgactgg ttcttctgga gacctcctaa
7381  gggttatgac gccgaaggca agccaattcc tccaaacaat tggaaatctt tcttggtgg
7441  ttcagcttgg acttttgatg aaactacaaa tgaattttac ctccgtttgt ttgcgagtcg
7501  tcaagttgac ttgaattggg agaatgaaga ctgcagaagg gcaatctttg aaagtgctgt
```

-continued

```
7561  tggattttgg ctggaccatg gtgtagatgg ttttagaatc gataccgctg gtttgtattc
7621  gaaacgtcct ggtttaccag attccccaat ttttgacaaa acctcgaaat tacaacatcc
7681  aaattggggg tctcacaatg gtcctaggat tcatgaatat catcaagaac tacacagatt
7741  tatgaaaaac agggtgaaag atggtagaga aataatgaca gtcggtgaag ttgcccatgg
7801  aagtgataat gctttataca ccagtgcagc tagatacgaa gtcagcgaag ttttctcctt
7861  cacgcacgtt gaagttggta cctcgccatt tttccgttat aacatagtgc ccttcacctt
7921  gaaacaatgg aaagaagcca ttgcatcgaa cttttttgttc attaacggta ctgatagttg
7981  ggctaccacc tacatcgaga atcacgatca agcccggtca attacgagat ttgctgacga
8041  ttcgccaaag taccgtaaaa tatctggtaa gctgttaaca ttgctagaat gttcattgac
8101  aggtacgttg tatgtctatc aaggtcagga gataggccag atcaatttca aggaatggcc
8161  tattgaaaag tatgaggacg ttgatgtgaa aaacaactac gagattatca aaaaaagttt
8221  tggtaaaaac tcgaaggaaa tgaaggattt ttttaaagga atcgccctac tttctagaga
8281  tcattcgaga actcccatgc catggacgaa agataagccc aatgctggat ttactggccc
8341  agatgttaaa ccttggtttc tcttgaatga atctttcgag caaggaatca atgttgagca
8401  ggaatccaga gatgatgact cagttctcaa ttttttggaaa agggccttgc aagccagaaa
8461  gaaatataag gaacttatga tttatggtta cgatttccaa ttcattgatt tagacagtga
8521  ccagatcttt agcttcacta aagagtacga agacaagacg ctgtttgctg ctttaaattt
8581  cagtggcgaa gaaattgaat tcagcctccc aagagaaggt gcttctttat cttttattct
8641  tggaaattat gatgatactg acgtttcctc cagagttttg aaaccatggg aaggtagaat
8701  ctacctcgtc aaataaaatt agtgccggct ttttttttagc gcgtacttta acgaaataac
8761  acatgatttt tcacatgatt tttgttagat aaatttttta tatgtaaatg atgatagcgt
8821  aaaagcactg ttgataattt gtttcaccat tatgggtaaa tgtgttttc tacatgaccc
8881  tcgttcatta tgatatttag cgtgtatata aatgtgaatt ccaaattatt aatgaggcat
8941  aagaagcact atccttttctc ttcggatgaa acaagggag aagaaacctg tgctggtatt
9001  aatgctgaaa tgtcttgcta agaatcatac aaggtggtag ttttatttaa taaagaaaag
9061  aaaaggacta gatataaaaa gtgaaatgaa tataagatag cgttaagaga tgtccgcagt
9121  acttgacaca taatttagcg ttttctcggg aagctctgtg attttatgat tcaataacac
9181  agcgtaattg atttcgtgat agttcgatcc tatatg
```

SEQ ID NO: 3. MAL2-8c Construct

```
FEATURES        Location/Annotation
misc_feature    1...500/"UPSTREAM_NLS2"
misc_feature    509...1406/"Upstream Mal6 ER"
misc_feature    1407...2813/"Mal2-8c CEN.PK122"
misc_feature    2814...3227/"Terminator Mal2-8c CEN.PK122"
misc_feature    3236...3735/"DOWNSTREAM_NLS2"

1  agaactttga ctcttctaca acgtgaatgc ctttgataag aatgaaattc caaaacaagt 61  aatgttggga ggtagatttc ctccactgct aattccaact acgtgtgcat ttttcaatag 121  taatattccg tcacaagagg cttatttttca ttttctctac cctcatcttt ttctcacttt 181  tttccttaca atgaatacat gtgatataga tacttaattg tctgttttgc gagcttgctt 241  cttcatatct atgtaatatg ggccaggtca acccaacatc taccaattat ctatatgaag 301  aaaaatatga ttggtagtta ccgccaatgc atagatttta gacaacttaa taaggccatg
```

-continued

```
 361   ttaaagggtg cattcccact atcgcgctta ggattggatg aagcataact tttcttcact
 421   gtcaaattgc atcgtagtta tatcagatcc aaataaaaaa tgaaaataac aataacaagc
 481   cttctatttt ttcttgtcat gtttaaacgg tcatggaaga cctgaactaa agtgttttag
 541   taaaccaatt ggagtgagag tttttcattc cgaagattct ttatctcaaa atttctttat
 601   cgaaagacac ttctgtgtca ctgtccgttc aatcagtcag atagttccaa ctccgatgtc
 661   ttccaatacc tcaacgaaga ccgaaaaata aaaggtttgt ttgacggagt gtgttgatta
 721   gtgcattggt gacgtggggt agcaaaatcc agatacttct attttttgaa aaagaaagga
 781   gagagtgcta gaatgttttc acgtttatca gtacacgaaa aacaaaacct gaagcaaatg
 841   attaccataa ctattgtcca cttatgggga agttgctaaa ataacacat tatttactaa
 901   gggaacacaa tttgctcata gtatacttga ctttttttac ttaacttttg cagcgattgg
 961   tgatgaaaat gagcatgcag actaataggt aggaaagtag aactacttag aaacattctc
1021   cttaagtgtt ttcaccacta agcattttat atttaattgt taaaaaatat atactattga
1081   agaaccactt tcctgaaata tcaagaacaa aaagtctgc actatggtcc cgcaattgat
1141   gcatttgaga attcttttaa ctcaatagta atatgcattg ttcttatcta aaaaattgca
1201   ggtacctgca gactaatccg ggtcatgatc tgcgctgcgc ccgtcatccc accccgtgct
1261   gcctgccact tgaagctacc ccgggtttaa taattcgttc tttaagttcc acaacttaaa
1321   tacaggcagc taaaaaactg ggttcgagag ttttccactt tatagacaaa ataaaaata
1381   ctgccagaaa atttatcata taataatatg ggtattgcga acagtcttg cgactgctgt
1441   cgcgttcgtc gagtaaagtg tgacaggaat aaaccatgta atcgctgcac tcagcgcaat
1501   ttgaactgca cttatcttca accgttgaaa aagagaggtc caaaatccat tagagcagga
1561   agcttaaaaa aaatagcgga agtgcagatg gtgagtatga ataataatat tatgaccgct
1621   ccggtggtat gtaagaaggt tccgaaaaac ctgattgatc aatgtttgag gttgtatcat
1681   gataacttat atgtaatttg gccaatgctt tcctacgatg atcttcacaa gcttttggag
1741   gaaaattatg aggactgcag cacttattgg tttctggtat ccctttcggc agctactctt
1801   agcgacttgc aaattgaaat agagtatgag gaaggagtca cttttactgg agagcagtta
1861   tgcactcttt gcatgttatc tcggcaattc tttgacgacc ttagtaacag cgacatattt
1921   cgaatcatga catactattg tttgcaccgt tgttacgcgc agtttgctga tacaagaact
1981   tcatacagac tttcttgtga ggctattggc ctcatcaaga tagctggatt ccatcgggaa
2041   gaaacctatg aattccttcc cttcggtgaa caacaactca gaaggaaagt ttactattta
2101   cttcttatga cagagagatt ttacgctgta tatattaagt gtgtcacgag cctagataca
2161   acaatagcgc caccactacc agaggttgta acagaccctc gtctttctct ggaaagcttc
2221   cttgaggtga ttagagtttt cactgtacct ggaaagtgtt tttatgatgc tttggctact
2281   aactgtgtcg atgattcctg caccgaagac tctctaaaaa ggatatgaa cgaacttcat
2341   accacatcac ttgatataga gccatggtct tatggctatg tggacatttc attttctcga
2401   cattggatta gggcgctggc ttggaagcta gtgtttcaga tgaatggtac caagtttttc
2461   tcaaacgcca ataatgctca catattggtc gaaattgcaa aggatatgct ggacgacata
2521   ttcttaactc caaacaacct gtatgatgta catggtcctg gaataccaat gaaatcattg
2581   gaagtagcca atgcattggt agatatcgta aataagtatg atcacaatat gaagttggag
2641   gcttggaata ttttgtgcga tgtatccaag ttcgtttttct ccctgaaaca ttgcaatcat
```

-continued

```
2701  aaaatgtttc aaaggttttc aactaaatgt cagagtgctc taatcgattt gcctatctct 2761  agaccactgc gcctaaatga tgattccaaa gatgaagacg acataattcc ttaatttatt 2821  gttcacgccg ttcacttata cgagatagat atactgatag agtgtgagtg atattcttaa 2881  gtcttgcttt tcgagggtgt aagaagctat gttcttcagg cgagattatt ctactcctgc 2941  cttacttgtt tgtaatattt agttctgatg gtcatgataa ttctatatac agttacatta 3001  agtatatact taagcgggca gcttactaat ataaattttg tggcatttt  gttgggatat 3061  gagaatcatg tatcgttgat ttacaaagcg aatttacgtt accaggaata gggaatactc 3121  tcttgaattc taacataagc acagaaatgc tgaaagaata cgtcaaaaag taaatttaca 3181  gaattaaaaa aaaaataatt gttgccggaa catgaataga gtgtatcagt ttaaacgcac 3241  actacttcat aatggtgcaa atttgccctc attacgtgat aacaccactc taactgatgc 3301  tcgtaatgtg ttaaagtact tacaagtgct tggttttcca agcaacaaaa tagcggctgc 3361  ggatactgtt ggaactctta tcatatttag caatcgtgcg gaagctaaca gtaccgctat 3421  gacgaagaca gtgtcatact gttatcgtaa ctacgggcat agtttttact tcactcatta 3481  caaatacgac tattttccta gtgagattag ttatatggca aaacttggcg atgccgccgt 3541  caaccatacg gacttacctc actttaggaa caacaaacgg ctaacaacgc aagaagtcaa 3601  tgccttccaa catccaattg tcgaatttta gtaagtgctc aggtattacg ttatgtacat 3661  gtatgatact tttgattaac atcctttata cacaaagatg tatgcatgaa tggtgcaaat 3721  atctcgacga tgcgca
```

SEQ ID NO: 4. Predicted Protein Product of MAL11 from
MAL1 Gene Cluster Sequence (Sequence Number 2)

```
  1  mkniislvsk kkaasknedk nisessrdiv nqqevfnted feegkkdsaf eldhlefttn 61  saqlgdsded nenvinemna tddaneanse eksmtlkqal lkypkaalws ilvsttlvme 121  gydtallsal yalpvfqrkf gtlngegsye itsqwqigln mcvlcgemig lqittymvef 181  mgnrytmita lglltayifi lyyckslami avggqilsaip wgcfqslavt yasevcplal 241  ryymtsysni cwlfgqifas gimknsqenl gnsdlgyklp falqwiwpap lmigiffape 301  spwwlvrkdr vaearkslsr ilsgkgaekd iqvdltlkqi eltiekerll asksgsffnc 361  fkgvngrrtr lacltwvaqn ssgavllgys tyfferagma tdkaftfsli qyclglagtl 421  cswvisgrvg rwtiltygla fqmvclfiig gmgfgsgssa sngagglla  lsffynagig 481  avvycivaei psaelrtkti vlaricynlm avinailtpy mlnvsdwnwg aktglywggf 541  tavtlawvii dlpettgrtf seinelfnqg vparkfastv vdpfgkgktq hdsladesis 601  qsssikqrel naadkc
```

SEQ ID NO: 5 Predicted Protein Product of MAL12 from
MAL1 Gene Cluster Sequence (Sequence Number 2)

```
  1  mtisdhpete pkwwkeatiy qiypasfkds nndgwgdlkg itsklqyikd lgvdaiwvcp 61  fydspqqdmg ydisnyekvw ptygtnedcf elidkthklg mkfitdlvin hcstehewfk 121  esrssktnpk rdwffwrppk gydaegkpip pnnwksffgg sawtfdettn efylrlfasr 181  qvdlnwened crraifesav gfwldhgvdg fridtaglys krpglpdspi fdktsklqhp 241  nwgshngpri heyhqelhrf mknrvkdgre imtvgevahg sdnalytsaa ryevsevfsf
```

```
301  thvevgtspf  frynivpftl  kqwkeaiasn  flfingtdsw  attyienhdq  arsitrfadd 361  spkyrkisgk  lltllecslt  gtlyvyqgqe  igqinfkewp  iekyedvdvk  nnyeiikksf 421  gknskemkdf  fkgiallsrd  hsrtpmpwtk  dkpnagftgp  dvkpwfllne  sfeqginveq 481  esrdddsvln  fwkralqark  kykelmiygy  dfqfidldsd  qifsftkeye  dktlfaalnf 541  sgeeiefslp  regaslsfil  gnyddtdvss  rvlkpwegri  ylvk
```

SEQ ID NO: 6. Predicted Protein Product of MAL13 from MAL1 Gene Cluster Sequence (Sequence Number 2)

```
  1  mtltkqtcak  qacdccrirr  vkcdgkrpcs  sclqnsldct  ylqpsrkrgp  ksirlrslkr 61  iaevqresgp  ntiatapviy  krvpkklidq  clrlyhdnly  viwpllsydd  lhklleekyn 121  dnyvywflta  lsaatlsdlq  teikseeevt  ftgkqlsnlc  isscqqfddl  dnsnifnimt 181  yyclhrsfaq  isnartsyrl  cceavglitv  aglhreetyg  sltfeeqqlr  rklyyllmt 241  eryyaiylhc  atsldatiap  pqlelvtdpq  lsmdsflemi  rvftvpgkcf  fdalaadstd 301  ascteeslkk  iwnelhttss  eiepwsngyi  disfsrhwir  ilawklayqm  rgsnfslnan 361  ngqipieiar  dmlidtyltp  enlydvhgpg  vpvktleiat  alvdivgqyd  hnmkleawnv 421  lhdvckfafs  lnhynndmlk  rfstkcqnal  itlpiskplq  ldgypkdned  idp
```

---

We claim:

1. A recombinant yeast strain comprising a strain of *S. cerevisiae* and an exogenous MAL1 gene cluster comprising a MAL11 gene, a MAL12 gene, and/or a MAL13 gene, wherein the strain of *S. cerevisiae* expresses the exogenous MAL1 gene cluster, wherein the exogenous MAL1 gene cluster comprises a sequence having at least 80, 85, 90, 95, or 98 percent homology to SEQ ID NO: 2; and wherein the recombinant yeast strain further comprises an exogenous MAL2-8c gene cluster, wherein the exogenous MAL2-8c gene cluster comprises a sequence having at least 80, 85, 90, 95, or 98 percent homology SEQ ID NO: 3.

2. The recombinant yeast strain according to claim 1, wherein the MAL1 gene cluster comprises a sequence having at least 85 percent homology to SEQ ID NO: 2 and the MAL2-8c gene cluster comprises a sequence having at least 85 percent homology SEQ ID NO: 3.

3. The recombinant yeast strain according to claim 1, wherein the MAL1 gene cluster comprises a sequence having at least 90 percent homology to SEQ ID NO: 2 and the MAL2-8c gene cluster comprises a sequence having at least 90 percent homology to SEQ ID NO:3.

4. The recombinant yeast strain according to claim 1, wherein the MAL1 gene cluster comprises a sequence having at least 95 percent homology to SEQ ID NO: 2 and the MAL2-8c gene cluster comprises a sequence having at least 95 percent homology to SEQ ID NO: 3.

5. The recombinant yeast strain according to claim 1, wherein the MAL1 gene cluster comprises a sequence having at least 98 percent homology to SEQ ID NO:2 and the MAL2-8c gene cluster comprises a sequence having at least 98 percent homology to SEQ ID NO:3.

6. The recombinant yeast strain according to claim 1, wherein the exogenous MAL1 gene cluster is overexpressed.

7. A vector, comprising:
a MAL1 gene cluster that comprises a sequence having 80, 85, 90, 95, 98, or 100 percent homology or identity to SEQ ID NO: 2.

8. A vector, comprising:
a MAL2-8c gene cluster that comprises a sequence having 80, 85, 90, 95, 98, or 100 percent homology or identity to SEQ ID NO: 3.

* * * * *